(12) United States Patent
Alborn, Jr. et al.

(10) Patent No.: US 7,169,919 B2
(45) Date of Patent: Jan. 30, 2007

(54) PROCESS FOR PREPARING LIPID II

(75) Inventors: William Ernest Alborn, Jr., Carmel, IN (US); Larry Chris Blaszczak, Indianapolis, IN (US); Scott Carl Mauldin, Indianapolis, IN (US); Paul Luther Skatrud, Greenwood, IN (US); Michael Scott VanNieuwenhze, Indianapolis, IN (US); Mohammad Sadegh Zia-Ebrahimi, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 748 days.

(21) Appl. No.: 09/833,647

(22) Filed: Apr. 18, 2001

(65) Prior Publication Data

US 2003/0027980 A1    Feb. 6, 2003

(51) Int. Cl.
C07H 1/06 (2006.01)
C07H 1/08 (2006.01)
C07H 5/04 (2006.01)
C07H 5/06 (2006.01)
C08B 37/00 (2006.01)

(52) U.S. Cl. .................. 536/128; 536/55.3; 536/123.1; 536/123.13; 536/124; 536/127

(58) Field of Classification Search ............... 536/18.7, 536/55.2, 55.3, 123, 123.1, 123.13, 124, 536/127, 128

See application file for complete search history.

(56) References Cited

U.S. PATENT DOCUMENTS

| | | | |
|---|---|---|---|
| 4,395,399 A | | 7/1983 | Ovchinnikov et al. |
| 5,141,674 A | * | 8/1992 | Leigh .......................... 252/305 |
| 5,506,204 A | | 4/1996 | Aston |

OTHER PUBLICATIONS

Van Heijenoort et al. Journal of Bacteriology (1992), vol. 174, pp. 3549-3557.*
Ye et al. J. Am. Chem. Soc. (2001), vol. 123, pp. 3155-3156.*
Schwartz et al. J. Am. Chem. Soc. (2001), vol. 123, pp. 11638-11643.*
C. Merser, et al., "Synthesis of the Repeating Disaccharide Unit of the Glycan Moiety of the Bacterial Cell Wall Peptidoglycan'" *Tetrahedron Lett.*, No. 13, pp. 1029-1032 (1973).
P.L. Durette, et al., "Synthesis of O- (2-acetamido-2-deoxy-β-D-glucosyl)—(1→4)-N-acetylmuramoyl-L-alanyl-D-isoglutamine, the repeating disaccharide-dipeptide unit of the bacterial cell-wall peptidoglycan", *Carbohydr. Res.*, vol. 77 pp. C1-C4 (1979).
S. Kusumoto, et al., "Chemical Synthesis and Biological Activities of Two Disaccharide Dipeptides Corresponding to the Repeating Units of Bacterial Peptidoglycan", *Bull. Chem. Soc. Jpn.*, vol. 59, pp. 1411-1417 (1986).
S. Kusumoto, et al., "Synthesis of β(1-4)—Linked Disaccharides of N-Acetylglucosamine and N-Acetylmuramic Acid by Their Direct Condensation" *Bull. Chem. Soc. Jpn.*, vol. 59, pp. 1419-1423 (1986).
J. Farkas, et al., "The Synthesis of O- (2-Acetamido-2-Deoxy-β-D-Glucopyranosyl)—(1→4)-N-Acetylnormuramoyl-L-α-Aminobutanoyl-D-Isoglutamine", *Carbohydr. Res.*, vol. 163, pp. 63-72 (1987).
M. Ledvina, et al., "An Alternative Synthesis of O- (2-Acetamido-2-Deoxy-β-D-Glucopyranosyl)—(1→4) -N-Acetylnormuramoyl-L-α-Aminobutanoyl-D-Isoglutamine", *Collect Czech. Chem. Commun.*, vol. 54, pp. 2784-2794 (1989).
A. Termin, et al., "Synthesis of the GlcNAcβ(1→4) MurNAcβ(1→4) GlcNAcβ(1→4) MurNAc Tetrasaccharide of Bacterial Peptidoglycan", *Liebigs Ann. Chem.*, pp. 527-533 (1992).
P.H. Gross, et al., "Stereochemically Pure Derivatives of Muramic and Isomuramic Acids", *Justus Liebigs Ann. Chem*, pp. 37-45 (1986).
M.P. DeNinno, et al., "A Method for the Selective Reduction of Carbohydrate 4,6-0-Benzylidene Acetals", *Tetrahedron Lett.*, vol. 36, pp. 669-672 (1995).
G-J Ho, et al., "Carbodiimide-Mediated Amide Formation in a Two-Phase System. A High-Yield and Low-Racemization Procedure for Peptide Synthesis", *J. Org. Chem*, 60, pp. 3569-3570 (1995).
M. Imoto, "Total Synthesis of *Escherichia coli* Lipid A, the Endotoxically Active Principle of Cell-Surface Lipopolysaccharide", *Bull. Chem. Soc. Jpn.*, vol. 60, pp. 2205-2214 (1987).
A.M. Palache, et al., "Adjuvancy and reactogenicity of N-acetylglucosaminyl-Nacetylmuramyl-dipeptide (GMDP) orally administered just prior to trivalent influenza subunit vaccine. A double-blind placebo-controlled study in nursing home residents", *Vaccine*, vol. 14, pp. 1327-1330 (1996).
R.M. Khaitov, et al., "Immunotherapy of Infectious Postoperative Complications with Glucosaminyl Dipeptide", *Immunotherapy of Infections Ed.*, pp. 205-211 (1994).
H. Brotz, et al., "The Lantibiotic Mersacidin Inhibits Peptidoglycan Synthesis by Targeting Lipid II", *Antimicrob. Agents Chemother.*, 42, 154-160 (1998).
Y. Van Heuenoort, et al., "Membrane Intermediates in the Peptidoglycan Metabolism of *Escherichia coli*: Possible Roles of PBP 1b and PBP 3", *J. Bacteriol.*, 174 (11), pp. 3549-3557 (1992).
S. Hitchcock, et al., "The First Total Synthesis of Bacterial Cell Wall Precursor UDP-N-Acetylmuramyl—Pentapeptide (Park Nucleotide)", *J. Am. Chem. Soc.*, 120, 1916-1917 (1998).
S. Kusumoto, et al., "Synthesis of N-Acetyl-β-D-Glucosaminyl—(1-4) -N-Acetylmuramyl-L-Alanyl-D-Isoglutamine", *Tetrahedron Lett.*, No. 45, pp. 4407-4410 (1978).
Whitesides, et al., "Synthesis of Glycosyl Phosphates Using the Fraser-Reid Activation", *J. Org. Chem.*, vol. 56, pp. 4547-4549 (1991).

(Continued)

*Primary Examiner*—Patrick Lewis
(74) *Attorney, Agent, or Firm*—John A. Cleveland, Jr.

(57) ABSTRACT

A process is described for preparing a substrate for the transglycosylase enzymes of bacterial cell wall biosynthesis. The chemical synthesis makes available a sustainable and substantially pure source of supply of lipid II, including analogs thereof, that may be used in the identification of new therapeutic agents capable of disrupting steps in bacterial cell wall biosynthesis.

13 Claims, 2 Drawing Sheets

OTHER PUBLICATIONS

Sabesan, et al., "Synthesis of glycosyl phosphates and azides", *Carbohydr. Res.*, vol. 223, pp. 169-185 (1992).

C. H. Wong, et al., "Synthesis and Use of Glycosyl Phosphites: An Effective Route to Glycosyl Phosphates, Sugar Nucleotides, and Glycosides", *J. Am. Chem. Soc.*, 115, pp. 2260-2267 (1993).

J.S. Anderson, et al, "Biosynthesis of the Peptidoglycan of Bacterial Cell Walls," *J. Biol. Chem.*, 242 (13), pp. 3180-3190 (1967).

H.G. Khorana, et al., "The Total Synthesis of Coenzyme A", *J. Am. Chem. Soc.*, 81, 1265 (1959).

H.G. Khorana, et al., "Nucleoside Polyphosphates. The Synthesis and Some Reactions of Nucleoside-5' Phosphoromorpholidates and Related Compounds. Improved Methods for the Preparation of Nucleoside-5' Polyphosphates", *J. Am. Chem. Soc.*, 83, pp. 649-657 (1961).

H.G. Khorana, et al., "Nucleoside Polyphosphates. An Improved General Method for the Synthesis of Nucleotide Coenzymes. Syntheses of Uridine-5', Cytidine-5' and Guanosine-5' Diphospate Derivatives", *J. Am. Chem. Soc.*, 83, pp. 659-663 (1961).

J. Wong, et al., "1H-Tetrazole as Catalyst in Phosphomorpholidate Coupling Reactions: Efficient Synthesis of GDP-Fucose, GDP-Mannose, and UDP-Galactose", *J. Org. Chem.*, 62, 2144-2147 (1997).

Imperiali, et al., "Synthesis of Dolichylpyrophosphate-Linked Oligosaccharides", *Tetrahedron Lett.*, 31, pp. 6485-6488 (1990).

J. K. Coward, et al., "Synthesis and Evaluation of Synthetic Analogues of Dolichyl-P-P-Chitobiose as Oligosaccharyltransferase Substrates", *Biorg. Med. Chem. Lett.*, 5, pp. 2701-2706 (1995).

R. W. Jeanloz, et al., Chemical Synthesis of Pyrophosphodiesters of Carbohydrates and Isoprenoid Alcohols. Lipid Intermediates of Bacterial Cell Wall and Antigenic Polysaccharide Biosynthesis, *Biochemistry*, 11, pp. 2565-2572 (1972).

A. R. Battersby, et al., "Studies on Specific Chemical Fission of Peptide Links. Part I. The Rearrangement of Aspartyl and Glutamyl Peptides", *J. Chem. Soc.*, 259 pp. 259-269 (1955).

E. Sondheimer, et al., "Imides from Asparagine and Glutamine. II. Alpha-Aminoglutarimide", *J. Am. Chem. Soc.*, 79, pp. 3767-3770 (1957).

D. Keglevic, et al., "Synthesis and Reactions of O-acetylated benzyl alpha-glycosides of 6-O (2-acetamido-2-deoxy-beta-D-glucopyranosyl) -N-acetylmuramoyl-L-alanyl-D-isoglutamine esters: The Base-Catalysed Isoglutamine • Glutamine Rearrangement in Peptidoglycan-Related Structures", *Carb. Res.*, 186, pp. 63-75 (1989).

D. Keglevic, et al., "Peptidoglycan-Related Disaccharide-Dipeptides: Differentiation Between Glutaminyl and Isoglutaminyl Residues by NMR Spectroscopy", *J. Carbohydrate Chem.*, 11, pp. 119-136 (1992).

G. Auger, et al., "Synthesis of an Analogue of the Lipoglycopeptide Membrane Intermediate I of Peptidoglycan Biosynthesis," *Letters In Peptide Science*, 4, pp. 371-376 (1997).

B. Schwartz, et al., "Lipid II: Total Synthesis of the Bacterial Cell Wall Precursor and Utilization as a Substrate for Glycosyltransfer and Transpeptidation by Penicillin Binding Protein (PBP) 1b of *Eschericia coli*," *J. Am. Chem. Soc.*, 123, pp. 11638-11643 (2001).

\* cited by examiner

FLUORESCENCE DETECTION OF GLYCAN

Lane 1: Dansyl Lipid II
Lane 2: Dansyl Lipid II + MtgA
Lane 3: Dansyl Lipid II + MtgA Lysozyme Digest
Lane 4:

PROCESS FOR PREPARING LIPID II

This application claims the benefit under 35 U.S.C. § 119(e) of prior co-pending U.S. provisional application Ser. No. 198,000, filed Apr. 18, 2000.

FIELD OF THE INVENTION

The present invention relates to a process for preparing substrates for the transglycosylase enzymes of bacterial cell wall biosynthesis and the substrates produced therefrom, in particular, the chemical synthesis of Lipid II and analogs thereof.

BACKGROUND OF THE INVENTION

Potent and notably non-toxic cell wall biosynthesis inhibitors have dominated treatment regimens for management of bacterial infections in both hospital and outpatient settings for more than fifty years. Recently, however, resistance of bacteria to these antibiotics has reached an alarming level and has begun to erode their once dependable clinical efficacy. Consequently, discovery of new drugs for the cell wall active antibacterial pharmacopoeia is urgently needed.

Cell wall (peptidoglycan) biosynthetic enzymes and their natural substrates can be very useful tools in studies directed to understanding resistance mechanisms at the molecular level or to the search for newer and more effective agents. Although the transpeptidase enzymes are well-known to be targets of the β-lactam antibiotics, studies on the transglycosylation process have been limited primarily due to poor accessibility of the natural transglycosylation substrate, Lipid II and its analogs. Isolation of Lipid II from liquid cultures of bacteria presents several formidable challenges, the most obvious being scale. The level of Lipid II has been estimated to be only 1,000–2,000 molecules per cell in *Esherichia coli*. Fifteen hundred molecules per cell equates to approximately 2.5 nM in a dense ($10^9$ cfu/ml) culture. Although 50 μg of $C^{14}$-Lipid II has been isolated from *Micrococcus luteus*, the amount isolated is minuscule, impure and radioactive. (see, i.e., Brotz, H., et al., *Antimicrob. Agents Chemother*, 42, 154 (1998).) Secondly, complete separation of the miniscule amount of Lipid II from relatively large amounts of cellular lipid and membrane components is very difficult. Hence, there is a need for an ample and sustainable supply of Lipid II to support any meaningful study of the transglycosylation process.

While Lipid II is a useful tool in the study of resistance mechanisms at the molecular level and the search for newer and more effective agents, it has other uses as well. For instance, Lipid II is useful in the quantitation of lysozyme, an enzyme that preferentially hydrolyzes the beta-1,4 glucosidic linkages between N-acetylmuramic acid and N-acetylglucosamine that occur, for example, in the mucopeptide cell wall structure of microorganisms such as *Micrococcus lysodeikticus*. In addition, certain lantibiotics can be purified by affinity chromatography on a resin containing immobilized Lipid II.

BRIEF SUMMARY OF THE INVENTION

The invention provides a process for preparing a lipid substrate (e.g., Lipid II analogs) that may be used as a substrate for transglycosylase enzymes of bacterial cell wall biosynthesis. The process includes the steps of:

(1) providing a protected disaccharide of formula 14

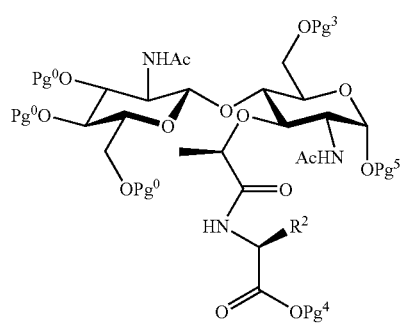

(2) introducing an anomeric phosphate to form a compound of formula 12

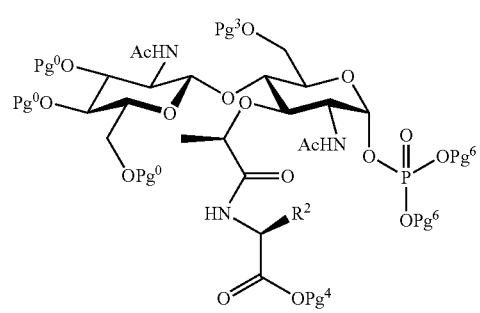

(3) introducing a peptide linkage to form a compound of formula 7

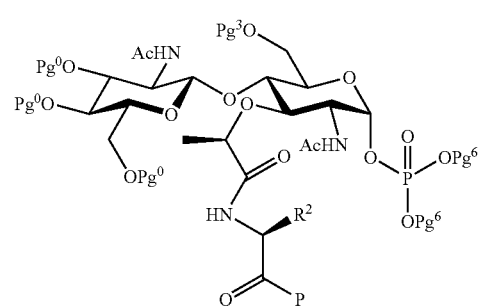

(4) introducing a lipid-carrier diphosphate linkage to form a compound of formula 2

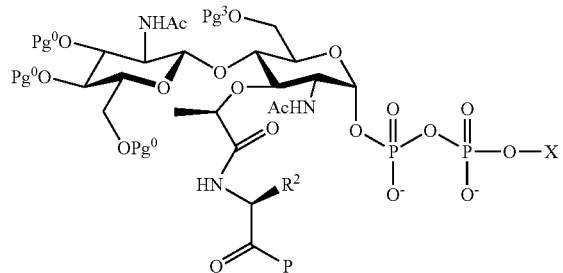

(5) removing the $Pg^0$ and $Pg^3$ groups and deprotecting the P group to produce a lipid substrate of formula 1

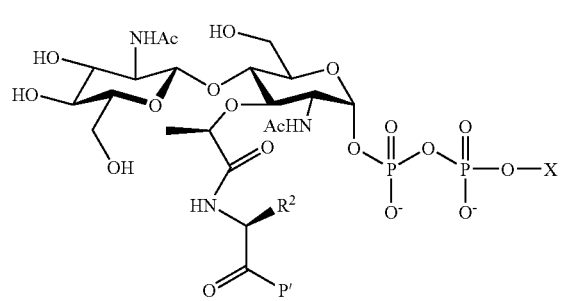

wherein:
- Ac is —C(O)CH$_3$;
- $Pg^0$ is an acyl hydroxy-protecting group;
- $Pg^3$ is an acyl hydroxy-protecting group;
- $Pg^4$ is a carboxy-protecting group;
- $Pg^5$ is a hydroxy-protecting group;
- $Pg^6$ is a phosphate-protecting group;
- $R^2$ is hydrogen, $(C_1–C_5)$ alkyl or $(C_1–C_3)$ alkylphenyl;
- X is a lipid carrier;
- P attached to the carbonyl is a residue of an amino acid or peptide, wherein P comprises a protected terminal carboxy group; and
- P' is a residue of an amino acid or peptide.

The invention also provides a chemical synthesis of Lipid II which provides a non-radioactive, sustainable supply having an isolated purity ≧50% (preferably ≧60%, 70% or 80%, more preferably ≧90% or 95%, even more preferably ≧98% or 99%, even more preferably ≧99.5%). The process for the preparation of Lipid II comprises the steps of:

(1) providing a protected disaccharide of formula 14

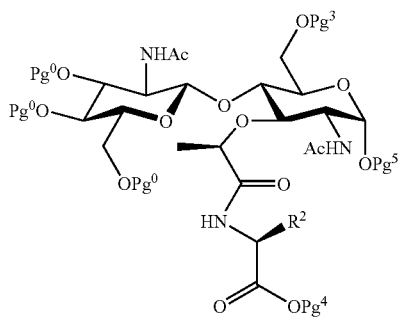

(2) introducing an anomeric phosphate to form a compound of formula 12

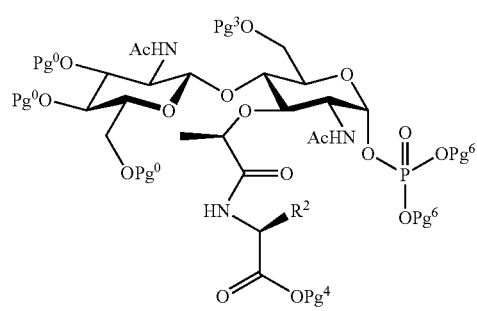

(3) introducing a peptide linkage to form a compound of formula 7a

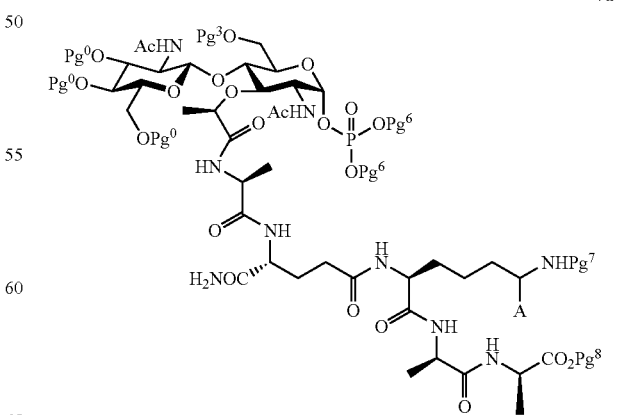

(4) introducing an undecaprenyl diphosphate linkage to form a compound of formula 2a

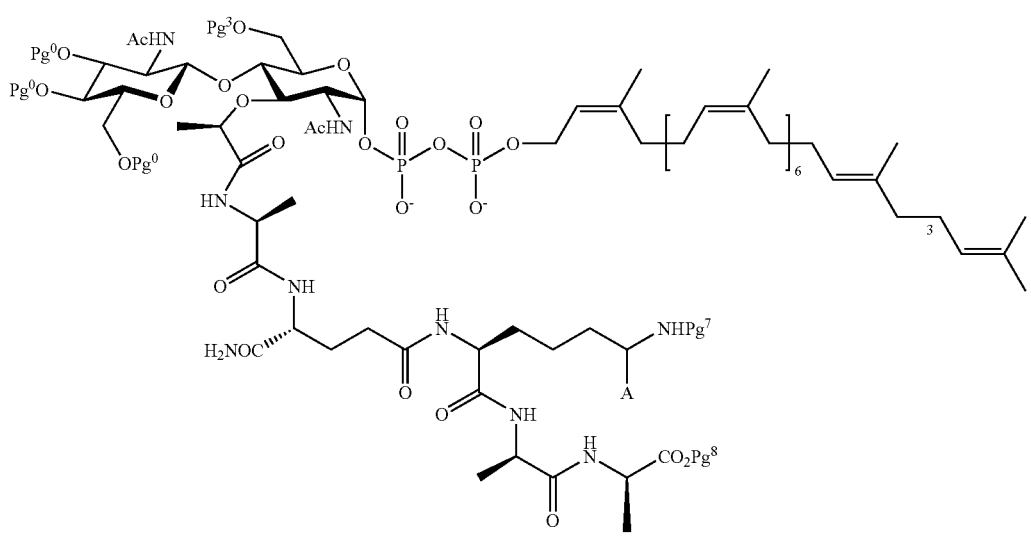

2a (5) removing $Pg^0$, $Pg^3$, $Pg^7$ and $Pg^8$ to form Lipid II;
wherein:
A is hydrogen or a carboxyl group;
$R^2$ is methyl;
Ac is —C(O)CH$_3$;
$Pg^0$ is an acyl hydroxy-protecting group;
$Pg^3$ is an acyl hydroxy-protecting group;
$Pg^4$ is a carboxy-protecting group;
$Pg^5$ is a hydroxy-protecting group;
$Pg^6$ is a phosphate protecting group;
$Pg^7$ is an amine-protecting group; and
$Pg^8$ is a carboxy-protecting group.

The invention further provides a substantially pure form of Lipid II. The Lipid II substrate is synthetically produced using the process described above and purified by means of chromatography.

Finally, the invention provides a process for isolating Lipid II, wherein the Lipid II is isolated at a pH greater than 6 (preferably from 6 to 12, more preferably from 7 to 10, even more preferably from 7 to 9).

DETAILED DESCRIPTION

Definitions

As used above, and throughout the description of the invention, the following abbreviations, unless otherwise indicated, shall be understood to have the following abbreviations:

| Designation | Reagent or Fragment |
| --- | --- |
| Ac | —C(O)CH$_3$ |
| AcOH | acetic acid |
| Ac$_2$O | acetic anhydride |
| BOC | t-butyloxycarbonyl |
| DBU | 1,8-diazabicyclo[5.4.0]undec-7-ene |
| TsOH | p-toluenesulfonic acid |
| NMM | N-methylmorpholine |
| THF | tetrahydrofuran |
| Bn | Benzyl (i.e., —CH$_2$Ph) |
| TFA | trifluoroacetic acid |
| Troc | 2,2,2-trichloroethoxycarbonyl |
| Cbz | benzyloxycarbonyl |

-continued

| Designation | Reagent or Fragment |
| --- | --- |
| TLC | thin layer chromatography |
| NMR | nuclear magnetic resonance |
| ESI-MS | electro-spray ionization mass spectrometry |
| EtOAc | ethyl acetate |
| IR | infrared spectroscopy |
| MeOH | methanol |
| NaOMe | sodium methoxide |
| NHS | N-hydroxysuccinimide |
| EDCI | 1-[3-(dimethylamino)propyl]-3-ethylcarbodiimide hydrochloride |
| Ph | phenyl |
| CDI | 1,1'-carboxyldiimidazole |
| h | hour(s) |
| Min | minutes |

As used above, and throughout the description of the invention, the following terms, unless otherwise indicated, shall be understood to have the following meanings:

"Amino acid" means an amino acid selected from the group consisting of natural and unnatural amino acids as defined herein. Amino acid is also meant to include—amino acids having L or D stereochemistry at the α-carbon. Preferred amino acids are those possessing an α-amino group. The amino acids may be neutral, positive or negative depending on the substituents in the side chain. "Neutral amino acid" means an amino acid containing uncharged side chain substituents. Exemplary neutral amino acids include alanine, valine, leucine, isoleucine, proline, phenylalanine, tryptophan, methionine, glycine, serine, threonine and cysteine. "Positive amino acid" means an amino acid in which the side chain substituents are positively charged at physiological pH. Exemplary positive amino acids include lysine, arginine and histidine. "Negative amino acid" means an amino acid in which the side chain substituents bear a net negative charge at physiological pH. Exemplary negative amino acids include aspartic acid and glutamic acid. Preferred amino acids are α-amino acids. Exemplary natural amino acids are isoleucine, proline, phenylalanine, tryptophan, methionine, glycine, serine, threonine, cysteine, tyrosine, asparagine, glutamine, lysine, arginine, histidine, aspartic acid and glutamic acid. "Unnatural amino acid"

means an amino acid for which there is no nucleic acid codon. Examples of unnatural amino acids include, for example, the D-isomers of the natural α-amino acids as indicated above; Aib (aminobutyric acid), βAib (3-aminoisobutyric acid), Nva (norvaline), β-Ala, Aad (2-aminoadipic acid), βAad (3-aminoadipic acid), Abu (2-aminobutyric acid), Gaba (γ-aminobutyric acid), Acp (6-aminocaproic acid), Dbu (2,4-diaminobutryic acid), α-aminopimelic acid, TMSA (trimethylsilyl-Ala), aIle (allo-isoleucine), Nle (norleucine), tert-Leu, Cit (citrulline), Orn, Dpm (2,2'-diaminopimelic acid), Dpr (2,3-diaminopropionic acid), β- or β-Nal, Cha (cyclohexyl-Ala), hydroxyproline, Sar (sarcosine), or the like; cyclic amino acids; $N^\alpha$-alkylated amino acids such as MeGly ($N^\alpha$-methylglycine), EtGly ($N^\alpha$-ethylglycine) and EtAsn ($N^\alpha$-ethylasparagine); and amino acids in which the α-carbon bears two side-chain substituents. The names of natural and unnatural amino acids and residues thereof used herein follow the naming conventions suggested by the IUPAC Commission on the Nomenclature of Organic Chemistry and the IUPAC-IUB Commission on Biochemical Nomenclature as set out in "Nomenclature of a-Amino Acids (Recommendations, 1974)" Biochemistry, 14(2), (1975). To the extent that the names and abbreviations of amino acids and residues thereof employed in this specification and appended claims differ from those noted, differing names and abbreviations will be made clear.

"Amino acid protecting group", and "peptide-protecting group" mean a group that protects an acid or amine moiety of the amino acid/peptide or other reactive moiety on the side chain of an amino acid/amino acid residue, e.g., hydroxy or thiol. For examples of "corresponding protected derivatives" of amino acid side chains, see T. W. Green and P. G. M. Wuts in "Protective Groups in Organic Chemistry" John Wiley and Sons, 1991. Protecting groups for an acid group in an amino acid are described herein in the section "carboxy-protecting group." Protecting groups for an amine group in an amino acid are described in the section "amine-protecting group."

"Amino acid residue" means the individual amino acid units incorporated into a peptide, or peptide portion of a molecule, through an amide linkage.

"Amine-protecting group" means an easily removable group that is known in the art to protect an amino group against undesirable reaction during synthetic procedures and to be selectively removable. The use of amine-protecting groups is well known in the art for protecting groups against undesirable reactions during a synthetic procedure and many such protecting groups are known, for example, T. H. Greene and P. G. M. Wuts, Protective Groups in Organic Synthesis, 2nd edition, John Wiley & Sons, New York (1991), incorporated herein by reference. Amine protecting group also includes acid-labile amine-protecting groups (e.g., BOC) and hydrogenation-labile amine-protecting groups (e.g., Cbz). A preferred $Pg^7$ amine-protecting group is trifluoroacetyl. In the present invention, $Pg^2$ is a group which does not lead to the generation of undesirable oxazoline by-products (i.e., $Pg^2$ cannot be an acyl group). Suitable $Pg^2$ amine-protecting groups include carbamate and imide groups. Particular imide groups include phthalimide, tetrachlorophthalimide and $(Ac)_2N$—. Particular carbamate groups include methoxy-carbonyl, 9-fluorenylmethoxycarbonyl, 2,2,2-trifluoroethoxycarbonyl, 2-trimethylsilylethoxy-carbonyl, vinyloxycarbonyl, allyloxycarbonyl, t-butyloxycarbonyl (BOC), 1,1-dimethyl-propynyloxycarbonyl, benzyloxycarbonyl (CBZ), p-nitrobenzyloxycarbonyl, 2,4-dichloro-benzyloxycarbonyl, trimethylsilyloxycarbonyl, 2,2,2-trichloroethoxycarbonyl, 1,1-dimethyl-2,2,2-trichloroethoxycarbonyl, or the like. A preferred $Pg^2$ amine-protecting group is 2,2,2-trichloroethoxycarbonyl.

"Carboxy-protecting group" means an easily removable group that is known in the art to protect an acidic hydrogen of a carboxyl group against undesirable reaction during synthetic procedures, e.g., to block or protect the acid functionality while the reactions involving other functional sites of the compound are carried out, and to be selectively removable. Such acid protecting groups are well known to those skilled in the art, having been extensively used in the protection of carboxyl groups, as described in U.S. Pat. Nos. 3,840,556 and 3,719,667, the disclosures of which are hereby incorporated herein by reference. For suitable acid protecting groups, see T. W. Green and P. G. M. Wuts in "Protective Groups in Organic Chemistry" John Wiley and Sons, 1991. Acid protecting group also includes hydrogenation labile acid protecting groups, such as benzyl. Examples of acid protecting groups include esters such as substituted and unsubstituted $C_1$ to $C_8$ alkyl, e.g., methyl, ethyl, t-butyl, methoxymethyl, methylthiomethyl, 2,2,2-trichloroethyl or the like, tetrahydropyranyl, substituted and unsubstituted phenylalkyl such as benzyl and substituted derivatives thereof such as alkoxybenzyl or nitrobenzyl groups or the like, cinnamyl, dialkylaminoalkyl, e.g., dimethylaminoethyl or the like, trimethylsilyl, substituted and unsubstituted amides and hydrazides, e.g., amides and hydrazides of N,N-dimethylamine, 7-nitroindole, hydrazine, N-phenylhydrazine or the like, acyloxyalkyl groups such as pivaloyloxymethyl or propionyloxymethyl or the like, aroyloxyalkyl such as benzoyloxyethyl or the like, alkoxycarbonylalkyl such as methoxycarbonylmethyl, cyclohexyloxycarbonylmethyl or the like, alkoxycarbonyloxyalkyl such as t-butyloxycarbonyloxymethyl or the like, alkoxycarbonylaminoalkyl such as t-butyloxycarbonylaminomethyl or the like, alkylaminocarbonylaminoalkyl, such as methylaminocarbonylaminomethyl or the like, acylaminoalkyl such as acetylaminomethyl or the like, heterocyclylcarbonyloxyalkyl such as 4-methylpiperazinyl-carbonyloxymethyl or the like, dialkylaminocarbonylalkyl such as dimethylaminocarbonyl-methyl or the like, (5-(lower alkyl)-2-oxo-1,3-dioxolen-4-yl)alkyl such as (5-t-butyl-2-oxo-1,3-dioxolen-4-yl) methyl or the like, and (5-phenyl-2-oxo-1,3-dioxolen-4-yl) alkyl such as (5-phenyl-2-oxo-1,3-dioxolen-4-yl)methyl or the like. Particular carboxy-protecting groups include methyl, 9-fluorenylmethyl, 2-(trimethylsilyl)ethyl, 2-(trimethylsilyl)ethoxymethyl, 2-methylthioethyl, 1,3-dithianyl-2-methyl, 2-(p-toluenesulfonyl)ethyl, 2-(p-nitrophenylsulfenyl)ethyl, 2-(2'-pyridyl)ethyl, 2-(diphenylphosphino)ethyl, p-(methylmercapto)phenyl, nitroethyl, allyl or the like. A preferred $Pg^4$ carboxy-protecting is —$CH_2CH_2SO_2Ph$. A preferred $Pg^8$ carboxy-protecting group is methyl.

"Hydroxy-protecting group" means an easily removable group that is known in the art to protect an hydroxyl group against undesirable reaction during synthetic procedures and to be selectively removable. The use of hydroxy-protecting groups is well known in the art for protecting groups against undesirable reactions during a synthetic procedure and many such protecting groups are known, for example, T. H. Greene and P. G. M. Wuts, Protective Groups in Organic Synthesis, 2nd edition, John Wiley & Sons, New York (1991), incorporated herein by reference. In the present invention, the $Pg^0$, $Pg^1$, and $Pg^5$ hydroxy-protecting groups are mutually orthogonal, as described herein. $Pg^1$ cannot be an electron-withdrawing group, since such groups deactivate the coupling reaction between the muramylamide compound of formula 18 and glucosopyranosyl compound of formula 17. Suitable $Pg^1$ groups include aralkyl, aralkenly and silyl groups. Particular aralkyl and alkenyl groups include benzyl and allyl, respectively. Particular silyl groups include trialkylsilyl groups, such as trimethylsilyl and (t-butyl)dimethylsilyl. Preferred $Pg^1$ groups are allyl and benzyl; a more preferred group is benzyl. Suitable $Pg^5$ groups include aralkyl and alkenyl. Preferred $Pg^5$ groups include allyl, n-pentenyl, and benzyl; a more preferred group is benzyl. In addition, $Pg^0$ and $Pg^3$ must be removable by saponification (i.e. $Pg^0$ and $Pg^3$ must be acyl groups). Particular acyl groups include formyl, acetyl, chloroacetyl, trichloroacetyl, o-nitrophenylacetyl, o-nitrophenoxy-acetyl, trifluoroacetyl, acetoacetyl, 4-chlorobutyryl, isobutyryl, o-nitrocinnamoyl, picolinoyl, acylisothiocyanate, aminocaproyl, benzoyl, or the like. Preferred $Pg^0$ and $Pg^3$ groups are chloroacetyl and acetyl; a more preferred group is acetyl.

"Phosphate-protecting group" means an easily removable group that is known in the art to protect a phospahte group against undesirable reaction during synthetic procedures and to be selectively removable. The use of phosphate-protecting groups is well known in the art for protecting groups against undesirable reactions during a synthetic procedure and many such protecting groups are known, for example, T. H. Greene and P. G. M. Wuts, Protective Groups in Organic Synthesis, 2nd edition, John Wiley & Sons, New York (1991), incorporated herein by reference. A preferred $Pg^6$ phosphate-protecting group is benzyl.

"Leaving group" of an activated ester means a substituent having sufficient lability such that it can be substituted by a good nucleophile (e.g., an amino group of a peptide unit). The lability of a particular substituent will vary depending upon substituents on the same and/or adjacent carbon atoms and the nature of the leaving group. Those skilled in the art will appreciate the types of leaving groups capable of substitution by an amino nucleophile. For suitable leaving groups, see M. Bodanszky and A. Bodanszky in "The Practice of Peptide Synthesis" Springer-Verlag, 1984; and M. Bodanszky in "Princliples of Peptide Synthesis", Springer-Verlag, 1984. In the present invention, for example, the leaving group activates the attached carbonyl such that the terminal amino acid group acts as a linker for linking the disaccharide with the peptide unit. Particular leaving groups include pentafluorophenoxy, N-oxysuccimide, N-oxyphthalimide, and N-oxybenzotriazole. A preferred leaving group is N-oxysuccinimide.

"Orthogonal protecting groups" means protecting groups for which there exists a set of conditions wherein one of the groups can be removed without removing the other(s). The term encompasses protecting groups for different moieties (e.g., orthogonal amine and hydroxy protecting groups) as well as the same moiety (e.g., orthogonal hydroxy-protecting groups). It is not a requirement that orthogonal protecting groups necessarily be different. For example, when the term is used to describe protecting groups for the same moiety, the groups may be different (e.g., orthogonal acetyl and benzyl hydroxy-protecting groups) or the same (e.g., orthogonal benzyl protecting groups).

"Electron-withdrawing group" means a group which is a more powerful electron attractor than hydrogen. Electron withdrawing groups exhibit negative inductive effects, whereas groups which are poorer electron attractors than hydrogen exhibit positive inductive effects. (see, e.g., E. S. Gould, Mechanism and Structure in Organic Chemistry, Holt, Rinehart and Winston, New York (1959), incorporated herein by reference).

"Acyl" means an R—C(O)— group, wherein R is bonded to the CO group through a carbon—carbon bond.

"Alkyl" means an aliphatic hydrocarbon group which may be straight or branched having about 1 to about 20 carbon atoms in the chain. Preferred alkyl groups have 1 to about 12 carbon atoms in the chain, more preferred is lower alkyl as defined herein. Branched means that one or more lower alkyl groups such as methyl, ethyl or propyl are attached to a linear alkyl chain. "Lower alkyl" means about 1 to about 4 carbon atoms in the chain that may be straight or branched.

"Alkenyl" means an aliphatic hydrocarbon group containing a carbon—carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain that may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Aryl" means an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

"Base of formula B" and "base of formula $B^{2}$" mean a compound comprising a $SP^2$ and $SP^3$ hybridized nitrogen having a non-bonded pair of electrons which is capable of being protonated. Examples of Bases of formula B or $B^1$ include compounds comprising optionally substituted imino, optionally substituted amino, and optionally substituted amidino groups.

"Carboxy" means an HO(O)C— (carboxylic acid or salt thereof) group.

"N-oxysuccinimide" means a moiety of the following structure

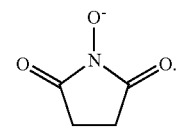

"Lipid carrier" means saturated and unsaturated hydrocarbon chains having more than one carbon. The chains may be straight or branched. The hydrocarbon may also be substituted (e.g., perfluorinated) or unsubstituted. Preferably, the hydrocarbon chain contains from 5 to 55 carbons and 1 to 11 prenyl units, more preferably 25 to 55 carbons and 5 to 11 prenyl units, most preferably 40 to 55 carbons and 8 to 11 prenyl units.

"Peptide" means a polymer encompassing amino acid residues joined together through amide bonds. Suitable peptide and polypeptide units include peptides containing 2 or more, preferably 2 to 4, amino acid residues. P can also be a single amino acid residue. P is preferably a polypeptide containing 4 amino acid residues. Particularly useful polypeptide units are D-iGln-L-Lys-D-Ala-D-Ala or D-iGln-Dap-D-Ala-D-Ala. Other combinations of amino acids and number of amino acids included in the amino acid or peptide unit may be used depending upon the enzyme selected to interact with the Lipid substrate. Suitable amino acid residues include natural amino acids, unusual amino acids and modified amino acids as defined in the World Intellectual Property Organization (WIPO) Handbook on Industrial Property Information and Documentation, Standard ST.25: Standard for the Presentation of Nucleotide and Amino Acid Sequence Listings in patent applications (1998), including Tables 1 through 6 in Appendix 2, incorporated herein by reference.

"Lipid II" means a compound of the following structure:

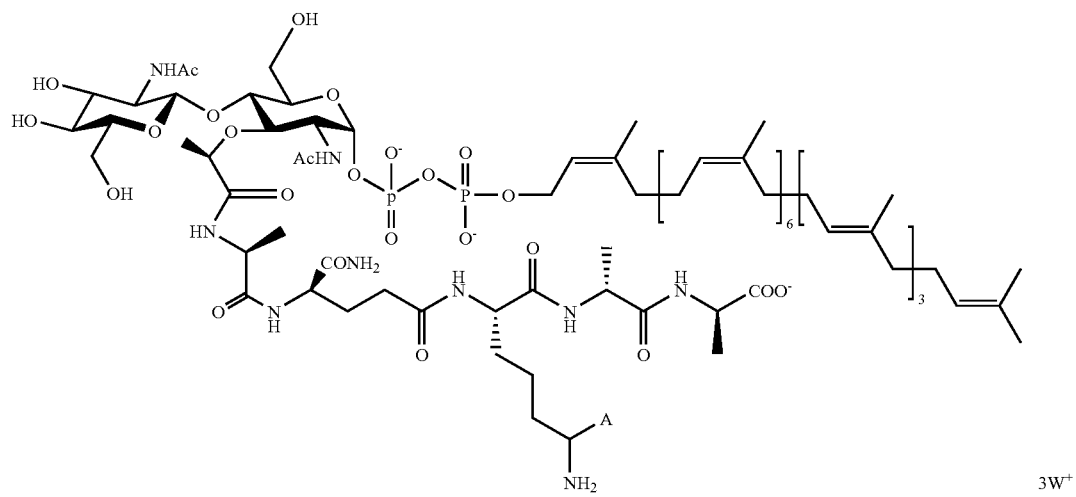

where A is a hydrogen or a carboxyl group (—CO$_2$H or salt thereof); Ac is —C(O)CH$_3$ and W$^+$ is each independently a proton or cation selected from the group consisting of an alkali metal (e.g., sodium or potassium), alkaline earth metal (e.g., magnesium or calcium), ammonium, alkyl ammonium (e.g., methyl ammonium or ethylammonium), and dialkyl ammonium (e.g., dimethyl ammonium, methylethylammonium or diethylammonium). Preferably, the pyrophosphate group is not protonated. For gram-positive Lipid II, A is generally hydrogen; whereas, for gram-negative Lipid II, A is generally a carboxyl group.

"Substantially pure" means an isolated purity of greater than or equal to 99% purity.

Figure 1:
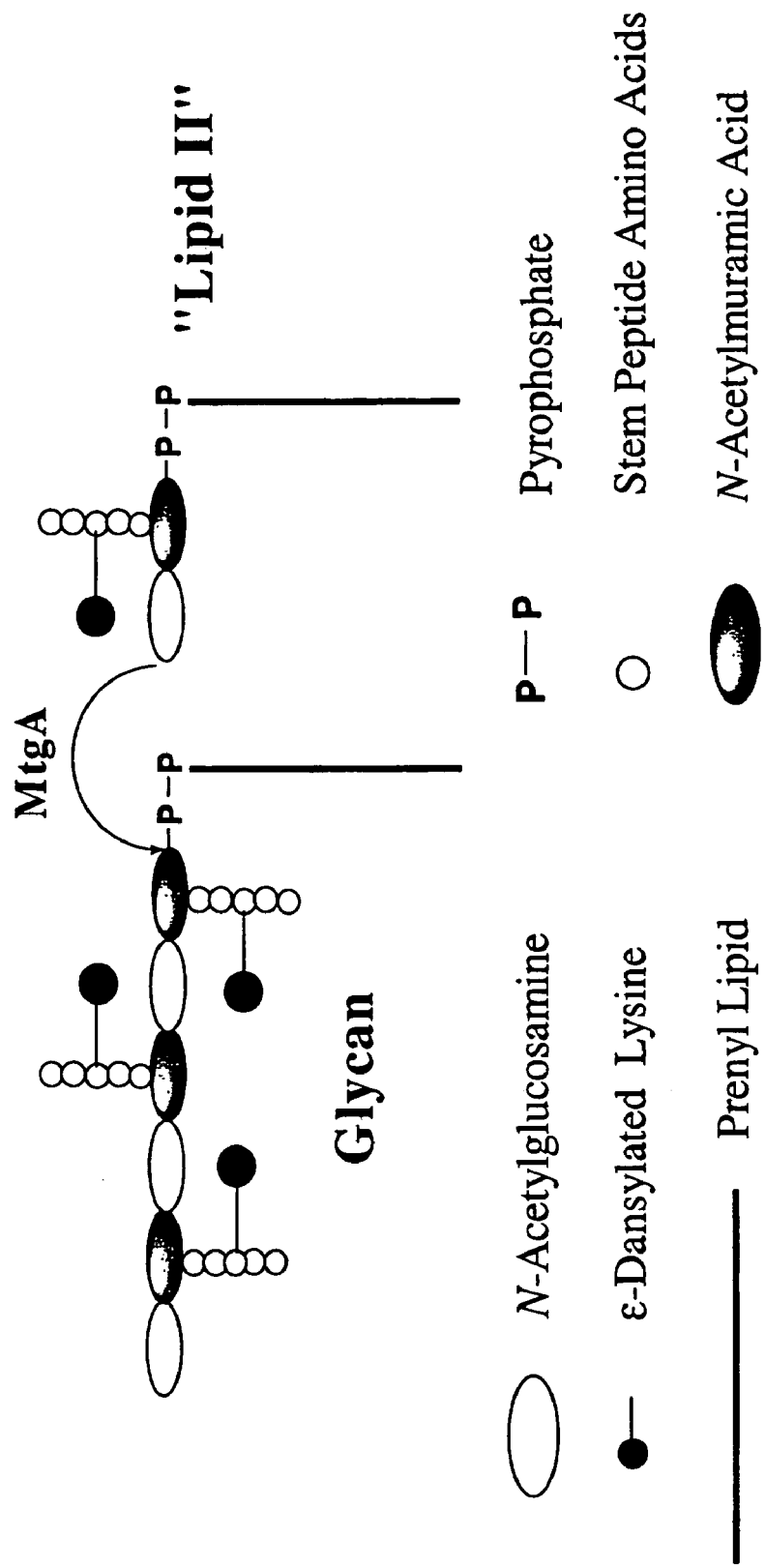
FIG. 1 illustrates the transglycosylation process using Lipid II as a substrate in cartoon form.
Figure 2:
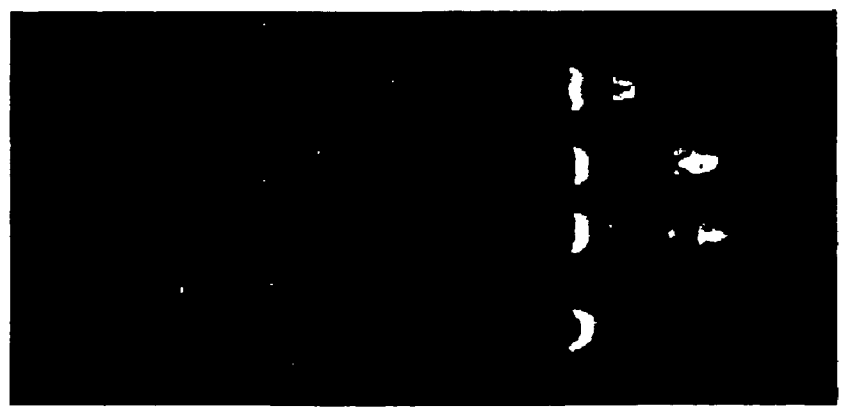
FIG. 2 illustrates the fluorescence detection of glycan strands generated by incubating a synthesized dansyl-tagged Lipid II derivative with a monofunctional transglycosylase (MtgA) from *Staphylococcus aureus*.

Utility of Lipid II and Analogs Thereof

I. Quantitation of Lysozome Using Lipid II

Lipid II is useful in the quantitation of lysozyme, an enzyme that preferentially hydrolyzes the beta-1,4 glucosidic linkages between N-acetylmuramic acid and N-acetylglucosamine that occur, for example, in the mucopeptide cell wall structure of microorganisms such as *Micrococcus lysodeikticus*.

Lysozyme may be the mediator in the anti-tumor function of macrophages (Osserman et al. (1973) *Nature* 243:331) which, it has been shown, secrete this enzyme (Gordon et al. (1974) *J. Exp. Med.* 139:1228). Cartilage lysozyme may play a role in cartilage calcification (Kuettner et al. (1974) *Biochim. Biophys. Acta* 372:335). There has been interest in lysozyme as a "natural" antibiotic, and as an aid in the diagnosis of disease (Glynn (1968) *Sci. Basis Med. Ann. Rev.* 31; Pruzanski et al. (1969) *Amer. J. Med. Sci.* 258:405). Elevated levels of serum and urinary lysozyme are present in monocytic and mono-myelocytic leukemia (Osserman et al. (1966) *J. Exp. Med.* 124:921; Brierre et al. (1974) *Clin. Chim. Acta* 50:265). The presence of this enzyme in cerebrospinal fluid is indicative of tumors of the central nervous system (Newman et al. (1974) *Lancet II* 756). Normally, lysozyme activity is practically absent from urine, bile, and spinal fluid (Hankiewicz et al. (1974) *Clin. Chim. Acta* 57:205). The enzyme is also used for lysing *E. coli* and *Streptomycetes* for extraction purposes (Haas et al. (1975) *Methods in Enzymology, XLIII* (Hash, J., ed.), Academic Press, N.Y., p. 621), such as extracting group specific antigen (Watson et al. (1975) *J. Clin. Microbiol.* 1:274).

Thus, lysozyme has a number of important medical and research implications and uses, and accurate quantitation thereof is therefore important in these applications.

Initially, lysozyme activity was estimated via a cell turbidimetric assay using *Micrococcus luteus* as a substrate. The rate of lysis of the cells by lysozyme is determined spectrophotometrically by measuring the decrease in turbidity of the cell solution. However, this method is not reliably reproducible due to lack of uniformity of *M. luteus* cell powder. The results also vary widely with buffer ionic strength differences.

Presently, a commercially available substrate for colorimetric assessment of lysozyme activity can be purchased from Sigma Chemical Company (St. Louis, Mo.). The substrate is the synthetic trimeric sugar, p-nitrophenyl beta-D-N,N',N"-triacetylchitotriose (PNP-(GlcNAc)$_3$) (Sigma Catalog product no. N-8638). Longer and shorter acetylchitooligo-saccharides have also been utilized for lysozyme assays, i.e., PNP-(GlcNAc)$_n$, where n=2–5. In all cases, the favored cleavage site for lysozyme results in the formation of PNP-GlcNAc. The activity measured in this assay is the increase in absorbance at 405 nm of the liberated p-nitrophenol. However, cleavage of the substrate by lysozyme to PNP-GlcNAc does not directly result in the liberation of p-nitrophenol. To obtain reliable colorimetric measurements of lysozyme activity, one must couple the assay to a second enzyme, β-N-acetyl-hexosaminidase (NAHase). NAHase cleaves PNP-GlcNAc to liberate p-nitrophenol, which is then quantitated (Nanjo et al. (1988) *J. Biochem.* 104: 255–258). This assay, while more accurate than earlier assays, still results in a high level of error due to lysozyme cleavage of the substrate that produces cleavage products other than PNP-GlcNAc. Also, two enzyme systems are less preferential than a system that directly measures the activity of interest. A new and improved assay that is highly accurate and easy to use would be valuable in laboratory settings for the routine determination of lysozyme in pharmaceutical/diagnostic preparations and biological materials. Such an assay can be utilized as an accurate diagnostic tool for the diagnosis of leukemia and tumors of the central nervous system. Detection of lysozyme activity in human serum, urine, or cerebrospinal fluid would quickly and accurately assist in the diagnosis of certain cancers, as noted above, and would be a valuable addition to the arsenal of cancer diagnostic tools. Lipid II can be used in lysozyme assays as follows.

Lipid II labeled with Oregon Green at the ε-amine of the lysine amino acid of the pentapeptide according to the manufacturer's instructions (Molecular Probes, Eugene, Oreg.) is a fluorescent molecule. This labeled Lipid II derivative can be polymerized using *Staphylococcus aureus* monofunctional transglycosylase A (MtgA; U.S. Pat. Nos. 6,143,868 and 5,922,540) into peptidoglycan strands that are non-fluorescent. Polymerization is achieved using 100 μM Oregon Green-labeled Lipid II, 5 μM MtgA, 50 mM MES (pH 5.9), 25 mM $MgCl_2$, 16.7 mM NaCl, and 0.27 mM CHAPS. Polymerization is complete after approximately 5 hours at 25° C.

The adjacent fluorophores (either neighboring dyes or those four repeating disaccharide units away) of the polymer interact when in close proximity, resulting in self-quenching. Addition of lysozyme to the labeled peptidoglycan material results in cleavage of the same bonds formed by MtgA in the polymerization reaction. Upon cleavage of these bonds, the dyes become physically separated, resulting in a loss of interaction between the dye molecules and a subsequent rise in fluorescence due to the decrease in self-quenching. Following the fluorescence of the lysozyme-catalyzed reaction (Excitation: 495 nm; Emission: 521 nm) over time compared to that of a standard curve permits one to quantitate the activity of the lysozyme present in the target preparation.

Thus, a lysozyme assay kit can contain pre-polymerized chains of Oregon Green labeled peptidogylcan, for which Lipid II is a mandatory starting material, size fractionated into lengths that immediately result in an increase in fluorescence upon initial lysozyme cleavage. For example, when cleaved, dimers are certain to result in an increase in fluorescence. Alternatively, peptidoglycan polymers can be labeled with Oregon Green such that the label moieties are spaced close enough to result in complete quenching, but sufficiently far apart that initial cleavage results in immediate relief of quenching. The amount of Oregon Green label incorporated into the polymer can be controlled by varying the ratio of labeled and non-labeled Lipid II used in the polymerization reaction. The labeled peptidoglycan can be present in the kit either as an aqueous solution or a solid powder. An aqueous solution of such Oregon Green labeled peptidoglycan can be prepared in a buffer of choice, and aliquots of the lysozyme preparation to be quantitated can then be added. Monitoring the increase in fluorescence intensity over time (Excitation 495 nm; Emission: 521 nm) and comparing the results to those obtained from a standard curve provides a quantitative measure of the lysozyme activity in the enzyme preparation.

II. Purification of Lantibiotics Using Lipid II

Lantibiotics are a class of peptide antibiotics characterized by specific post-translational modifications that result in the formation of the rare thioether amino acids lanthionin and/or 3-methyl-lanthionin within these molecules, hence the name "lantibiotics" (lanthionin-containing antibiotics). The lantibiotics epidermin, gardimycin (actagardine), mersacidin, and nisin possess antibacterial activity against gram-positive organisms.

Commercially, Nisin Z has been used as a food preservative for several decades, particularly in the dairy industry. It is nontoxic to humans, and the development of resistance to this antibiotic has not been observed despite its prolonged use. Nisin Z is presently being considered as both a drug candidate for human use and for inclusion in medical devices and surfaces of food processing machines to prevent microbial growth. Epidermin, gardimycin, and mersacidin are potentially useful as antibacterial drugs for the treatment of bacterial infections in humans.

Epidermin, mersacidin, and nisin specifically interact with Lipid II (Broetz et al. (2000) *Journal of Antimicrobial Chemotherapy* 46:1–6; Breukink et al. (1999) *Science* 286: 2361–2364; Broetz et al. (1998) *Antimicrobial Agents and Chemotherapy* 42(1):154–160). While there is no direct evidence for the binding of gardimycin to Lipid II, such binding is expected to occur in view of the structural similarities between gardimycin and mersacidin. One would therefore fully expect that all these lantibiotics can be purified from a mixture of compounds, such as a culture supernatant from a lantibiotic-producing microbial strain, by affinity chromatography on a resin containing immobilized Lipid II. Examples of lantibiotic-producing strains include *Lactococcus lactis* ssp. *lactis* (nisin); *Staphylococcus epidermidis* (epidermin); *Bacillus* sp. Strain HIL Y-85,54728 (mersacidin); and *Actinoplanes liguriae* (gardimycin). For this purpose, Lipid II is coupled to activated resins, for example those commercially available from suppliers such as Amersham Pharmacia Biotech. Coupling is performed according to the manufacturer's instructions. Generally, a solution of the desired ligand, in this case Lipid II, is simply mixed with a suspension of the activated resin in a suitable solvent or buffer (determined by the solubility of the ligand and by the coupling chemistry used), incubated, and excess Lipid II ligand is washed away.

If this method of coupling results in an orientation of Lipid II relative to the surface of the resin that does not allow binding of lantibiotics, then Lipid II is bound to hydrophobic beads to overcome this problem. In this way, Lipid II is presented the same way it is found in its natural membrane environment. A monolayer of Lipid II is formed on hydrophobic beads as described for a phospholipid monolayer by Retzinger et al. ((1985) *Analytical Biochemistry* 150:131–140) or Kim et al. ((1997) *Analytical Biochemistry* 250(1):109–116). For example, polystyrene-divinylbenzene beads are sonicated together with Lipid II in hexane/ethanol (approx. 1/1, v/v), and dried. The beads are redispersed in water, and washed with water, resulting in a lipid monolayer on the surface of the hydrophobic beads. If the molecular shape of Lipid II is incompatible with the formation of a Lipid II-only monolayer on the surface of the beads, the beads are coated with a mixture of phospholipids and Lipid II.

The lantibiotic-containing mixture is then passed through the column containing Lipid II resin under conditions that allow binding of the lantibiotics to the immobilized Lipid II. For example, conditions shown (Broetz et al. (1998) *Antimicrobial Agents and Chemotherapy* 42(1):154–160) to allow the binding of mersacidin, and presumably gardimycin, to Lipid II include:

a) 50 mM Tris-HCl, pH 7.8, 10 mM $MgCl_2$, 23° C.; or
b) half-concentrated Mueller-Hinton broth.

Conditions under which epidermin and nisin bind to Lipid II (Broetz et al. (1998) *Molecular Microbiology* 30(2): 317–327) include:

a) 69 mM Tris-HCl, pH 8.8, 58 mM $MgCl_2$, 11.6 mM $NH_4Cl$, 5.8 mM SDS; or
b) 10 mM Tris-HCl, pH 7.2, 0.85% NaCl.

Additional conditions under which nisin binds to Lipid II (Wiedemann et al. (2001) *Journal of Biological Chemistry* 276(1):1772–1779) include 25 mM MES-KOH, pH 6.0, 50 mM $K_2SO_4$, or 50 mM MES-KOH, pH 6.0, 100 mM $K_2SO_4$.

Unbound, non-lantibiotic materials are removed by eluting the column with the same buffer used for lantibiotic binding to resin-immobilized Lipid II.

It is fully expected that mersacidin and gardimycin can be eluted from the column by washing the resin with a buffer, e.g., 50 mM Tris-HCl, pH 7.8, containing EDTA, to remove divalent cations. Alternatively, bound Lipid II can be acid-hydrolyzed in order to break the bond between MurNAc and phosphate, generating fragments that no longer interact with mersacidin or gardimycin.

It is also fully expected that the interactions of nisin and/or epidermin with Lipid II covalently bound to the resin are broken with an organic solvent e.g., 100% acetonitrile, or a detergent. Extreme pH, high salt concentrations, or aqueous buffers containing EDTA can also be employed.

Overview of Synthetic Approach

The diversity of structural elements resident in Lipid II present several significant challenges for total synthesis. The central core of Lipid II consists of a [1,4]-linked disaccharide containing N-acetylglucosamine (NAG) and N-acetylmuramic acid (NAM) subunits. The muramyl residue is further decorated with a pentapeptide chain (e.g., L-Ala-D-iGln-L-Lys-D-Ala-D-Ala or L-Ala-D-iGln-meso-DAP-D-Ala-D-Ala) attached to the 3-position via a lactyl linkage, as well as a chemically sensitive undecaprenyl-linked α-glycosyl diphosphate moiety.

The synthesis of the central disaccharide core fragment itself in orthogonally protected form presented a significant synthetic challenge. For example, identification of a protective scheme having triple orthogonality is highly desirable to accomplish selective unmasking of the three types of pendant hydroxyl groups (i.e., anomeric OH, peripheral OH, and carboxyl OH). In addition, the stereoselective construction of the β-[1,4] glycosidic linkage was expected to be difficult irrespective of the method used to generate a reactive glycosyl cation donor. For example, with respect to the glycosyl cation, each of the following inherent properties contribute to a loss of reactivity of the glycosyl cation acceptor; (i) the intrinsic lack of nucleophilicity of the C(4)-hydroxyl group of glucopyranose-based acceptors, (ii) additional steric crowding around the C(4)-hydroxyl of muramic acid-based acceptors, and (iii) additional electronic deactivation of 2-deoxy-2-acylaminoglucopyranose acceptors relative to their glucopyranose-based counterparts. With respect to the glycosyl cation donor, an activation method with a predisposition toward formation of a β-[1,4] glycosidic linkage was needed. The reaction conditions for glycosyl cation generation also need to be compatible with functionality resident in both the donor and acceptor. Each of the synthetic issues associated with stereoselective construction of a NAG-NAM disaccharide precursor (see Scheme II below) have been addressed and a protocol for its synthesis on a multiple gram scale in fully differentiated form was developed. The synthetic process for the preparation of the NAG-NAM disaccharide precursor is exemplified in the Examples. The disaccharide core may alternatively be prepared using the general procedures described in Kantoci, D., et al., *Carbohydrate Research*, 162, 227 (1987).

In addition to the synthesis of the disaccharide core, Applicants have also successfully addressed other challenges in the total synthesis of Lipid II which include: (1) a method for introduction of an anomeric phosphate onto a suitably protected disaccharide precursor in an α-selective manner, (2) a mild method for introduction of the chemically sensitive undecaprenyl-linked diphosphate, (3) orthogonality of protective groups employed in the pentapeptide side chain and the carbohydrate periphery with those utilized to temporarily mask reactive functionality at the anomeric center of the muramyl fragment, (4) coordination of the entire protective group scheme to allow global deprotection under mild reaction conditions as the final step in the synthesis, and (5) development of a high performance liquid chromatography (HPLC) protocol for purification of the final product. The synthesis of Lipid II described below successfully addresses each of the issues outlined above.

Introduction of the undecaprenyl-linked diphosphate moiety at the later stage in the synthesis provided distinct advantages. For example, it avoided potential solubility complications in subsequent reactions that could arise from the enhanced lipophilic character of the undecaprenyl-linked substrate. In addition, late stage introduction of the lipid-linked diphosphate also minimized the number of subsequent synthetic operations that the chemically sensitive allylic diphosphate linkage had to withstand.

Applicants also discovered that the use of base-cleavable protective groups for all functional groups that are unmasked subsequent to their incorporation allowed them to avoid any potential acid sensitivity of the anomeric diphosphate.

Decomposition of the Lipid II intermediate due to the acid sensitivity of the pyrophosphate group has not been fully recognized in the art. Applicants discovered that once the pyrophosphate moiety was present in the compound by-products from decomposition could be minimized by maintaining a pH greater than about 6. Preferably the pH is maintained from 6 to 12, more preferably from 7 to 10, even more preferably from 7 to 9. It is believed that even the natural product could be isolated in higher yields and purity if the pH was maintained at a pH greater than 6 instead of the current practice of using 6M pyridinum/acetate in the isolation procedure which has a pH of 4.2. For a detailed description of the current isolation procedures for the natural product, see: Van Heuenoort, Y., et al., "Membrane Intermediates in the Peptidoglycan Metabolism of *Escherichia coli*: Possible Roles of PBP 1b and PBP 3," *J. Bacteriol.*, 174(11), 3549–3557 (1992); and Anderson, J. S., et al., "Biosynthesis of the Peptidoglycan of Bacterial Cell Walls," *J. Biol. Chem.*, 242(13), 3180–3190 (1967).

The Lipid II may be purified using conventional chromatography procedures well-known to those skilled in the art. A particular useful set of chromatography conditions is illustrated in the examples. The Lipid II is isolated in purities much higher than currently available. One may isolate the Lipid II in purities greater than 50%. Generally, the Lipid II may be isolated in greater than or equal to 60%, 70%, 80%, 90%, 95%, or 98% purity and under optimum conditions in substantially pure form ($\geq$99%).

It is to be understood that this invention covers all appropriate combinations of the particular and preferred groupings, and individual or combination of process steps as referred to herein.

General Preparation of Lipid II Analogs

A compound of formula 1, wherein the variables are as described herein, may be prepared by removing the $Pg^0$ and $Pg^3$ groups and deprotecting the P group a compound of formula 2, wherein the variables are as described herein,

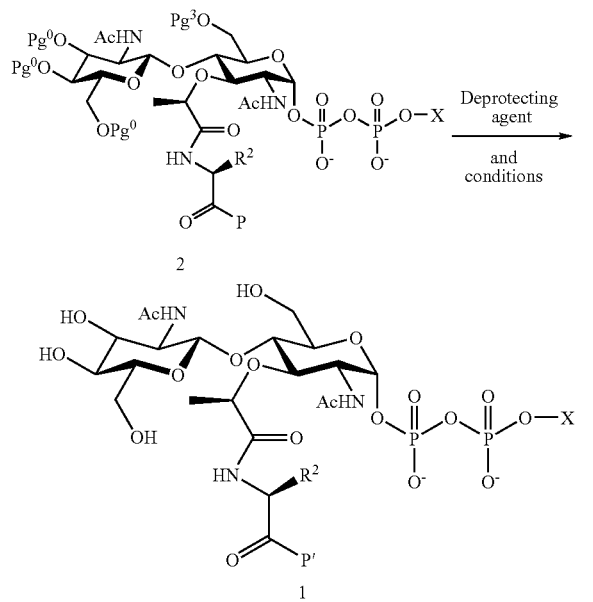

in the presence of a deprotecting agent under appropriate conditions. Particular $Pg^0$ and $Pg^3$ groups are acetyl, or the like. A particular deprotecting agent is aqueous sodium hydroxide, or the like. Particular deprotecting conditions encompass carrying out the deprotection in about a 1:1 solution of 1,4-dioxane:water, or the like, while stirring for about 2 h.

A compound of formula 2, wherein the variables are as described herein, may be prepared by treating an activated phosphate of formula 4, wherein $L^1$ is a leaving group and the other variables are as described herein, with a monophosphate of formula 3, wherein $B^2$ is a base and X is as described herein, under appropriate coupling conditions.

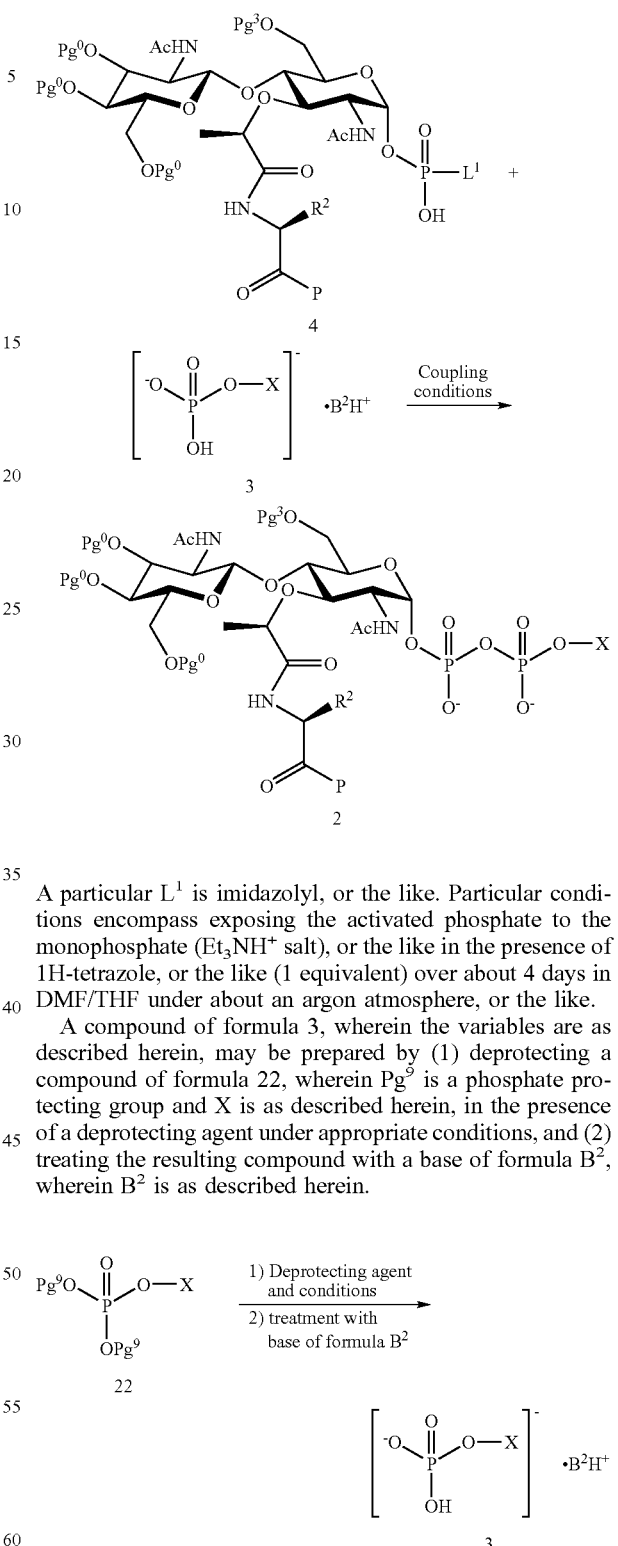

A particular $L^1$ is imidazolyl, or the like. Particular conditions encompass exposing the activated phosphate to the monophosphate ($Et_3NH^+$ salt), or the like in the presence of 1H-tetrazole, or the like (1 equivalent) over about 4 days in DMF/THF under about an argon atmosphere, or the like.

A compound of formula 3, wherein the variables are as described herein, may be prepared by (1) deprotecting a compound of formula 22, wherein $Pg^9$ is a phosphate protecting group and X is as described herein, in the presence of a deprotecting agent under appropriate conditions, and (2) treating the resulting compound with a base of formula $B^2$, wherein $B^2$ is as described herein.

A particular $Pg^9$ phosphate-protecting group is 2,2,2-trichloroethyl, or the like. A particular base of formula $B^2$ is triethylamine, or the like. A particular deprotecting agent is Zn dust, or the like, in the presence of a proton source (e.g., HCl), or the like. Particular conditions encompass adding 0.1 M HCl, or the like in THF (2–5 mL), or the like dropwise in two portions over about an hour to a stirred solution or suspension in THF, or the like of the compound of formula 22 (about 1 equiv) and zinc dust (about 12 equiv), or the like at about 0° C. The reaction mixture is stirred at about 0° C. and followed to completion by TLC. Upon completion, the reaction mixture is partitioned between Et$_2$O, or the like and 1N HCl, or the like, and stirred until the zinc dust, or the like is completely dissolved. The phases are separated and the aqueous phase extracted with Et$_2$O (x3), or the like. The combined Et$_2$O layers are dried with Na$_2$SO$_4$ and filtered. Triethylamine, or the like (1–3 mL), or the like is added and the organic phase concentrated in vacuo to yield compound 3 (80–95%).

A compound of formula 22, wherein the variables are as described herein, may be prepared by coupling a compound of formula 23, wherein L$^3$ is a leaving group and Pg$^9$ is as described herein, with a lipid alcohol of formula 24, wherein X is as described herein, under appropriate conditions.

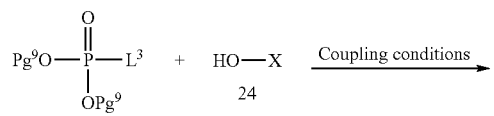

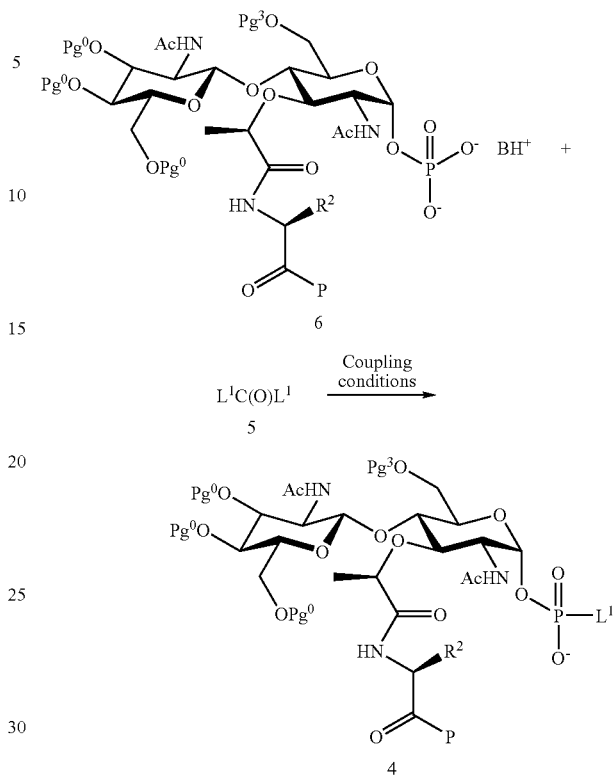

A particular -L$^3$ group is Cl, or the like. A particular Pg$^9$ group is 2,2,2-trichloroethyl, or the like. Particular conditions encompass adding the compound of formula 23 (about 1.5 equiv) and N,N-dimethylamino-pyridine (about 0.2 equiv), or the like, to a solution of the lipid alcohol (about 1 equiv), or the like, in anhydrous CH$_2$Cl$_2$ (about 0.1 M), or the like. Triethylamine (about 3 equiv), or the like is added dropwise and the reaction stirred at room temperature. After completion of the reaction as evidenced by TLC, the reaction mixture is partitioned between CH$_2$Cl$_2$, or the like and 1 N HCl, or the like. The aqueous layer is extracted with CH$_2$Cl$_2$ (x3), or the like. The organic layer is washed sequentially with H$_2$O and brine, or the like, dried (Na$_2$SO$_4$), or the like, and concentrated in vacuo. The residue is purified by flash chromatography over silica gel eluting with a gradient of hexanes to about 10% EtOAc in hexanes. Concentration of relevant fractions affords the compound of formula 22 (about 80–about 90%) as a colorless oil.

A compound of formula 4, wherein the variables are as described herein, may be prepared by coupling a compound of formula 6, wherein B is a base and the other variables are as described herein, with an activating agent of formula 5 under appropriate conditions.

The coupling reaction initially yields a phosphate diester intermediate, which gives off CO$_2$ to yield the activated phosphate of formula 4. A particular activating agent is CDI, or the like. A particular base counter ion BH$^+$ is C$_5$H$_5$NH$^+$, or the like. Particular conditions encompass carrying out the reaction in anhydrous DMF/THF, or the like for about 2 h. Electrophilic activation of the anomeric phosphate by conversion to the corresponding phosphorimidazolate derivative is described in Fang, X., et al., *Bioorg. Med. Chem. Lett.*, 5, 2701 (1995).

A compound of formula 6, wherein the variables are as described herein, may be prepared by (1) removing the Pg$^6$ groups of a compound of compound of formula 7, wherein the variables are as described herein, in the presence of a hydrogenation agent under appropriate conditions, and (2) treating the resulting compound with a base of formula B to form a phosphate salt.

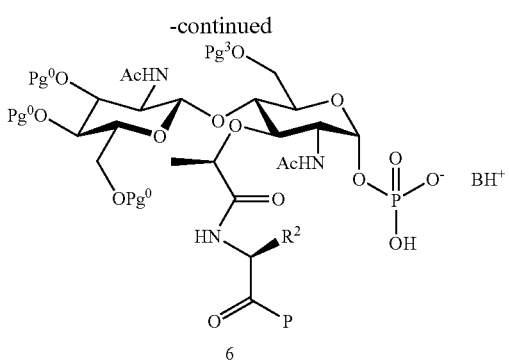

6

A particular Pg⁶ group is benzyl, or the like. A particular hydrogenation agent is Pd/C, or the like. Particular hydrogenation conditions encompass adding the compound 7 to a suspension of about 10% Pd/C, or the like in an alcohol (preferably methanol), or the like cooled in an ice bath to aid in degassing the reaction solution. The solution is then warmed to room temperature and hydrogenated at atmospheric pressure for about 1.5 h. A particular base of formula B is pyridine, or the like.

A compound of formula 7, wherein the variables are as described herein, may be prepared by coupling an activated ester of formula 9, wherein —OL is a leaving group and the other variables are as described herein, with an amino acid/peptide of formula 8, wherein P is as described herein, under appropriate conditions.

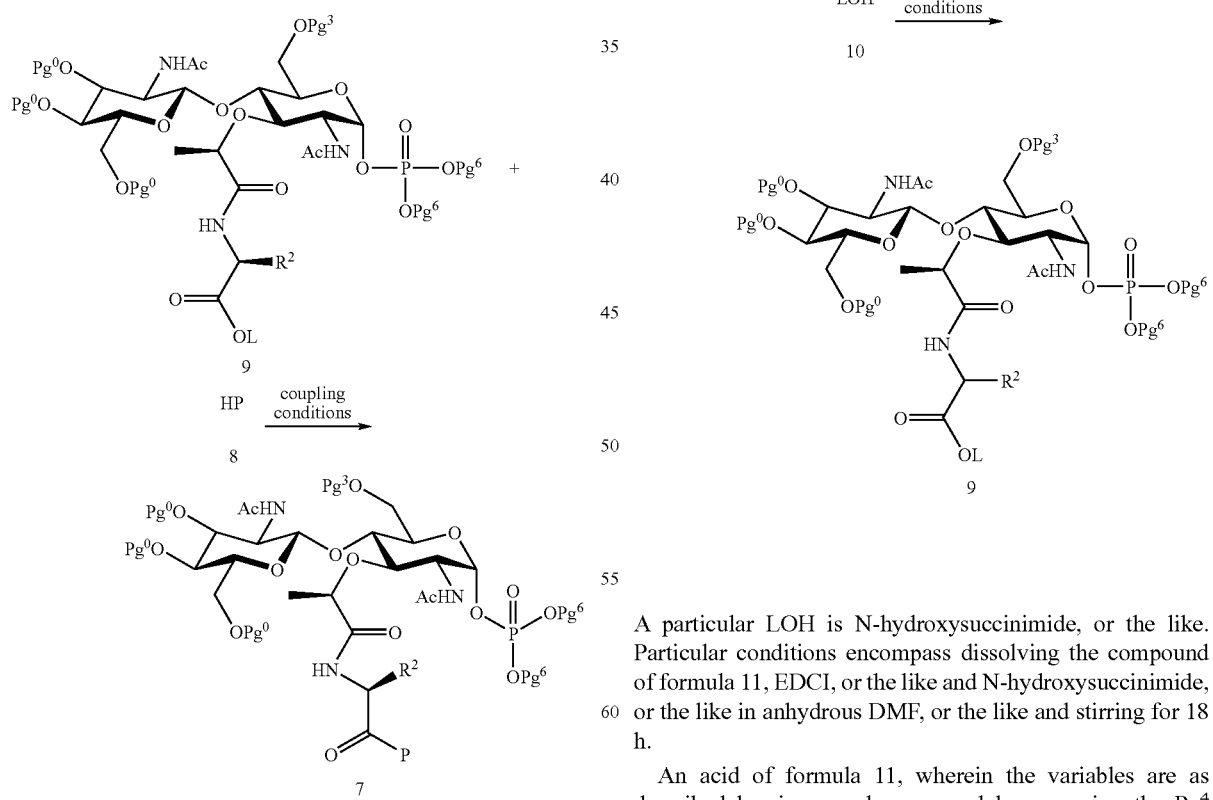

A particular —OL is N-oxysuccinimide, or the like. Particular conditions encompass dissolving the compounds of formulas 8 and 9, along with iPr₂NEt, or the like, in DMF, or the like and stirring at about room temperature under argon, or the like for 18 h.

A compound of formula 8, wherein the variables are as described herein, is prepared via conventional peptide synthetic methods known in the art.

An activated ester of formula 9, wherein the variables are as described herein, may be prepared by esterifying an acid of formula 11, wherein the variables are as defined herein, with a compound of formula 10 under appropriate conditions.

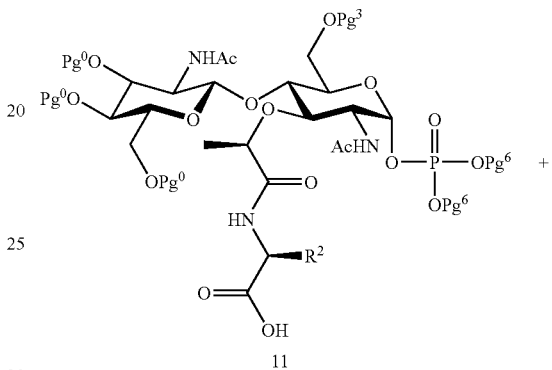

A particular LOH is N-hydroxysuccinimide, or the like. Particular conditions encompass dissolving the compound of formula 11, EDCI, or the like and N-hydroxysuccinimide, or the like in anhydrous DMF, or the like and stirring for 18 h.

An acid of formula 11, wherein the variables are as described herein, may be prepared by removing the Pg⁴ group of a compound of formula 12, wherein the variables are as described herein, in the presence of a carboxy-deprotecting

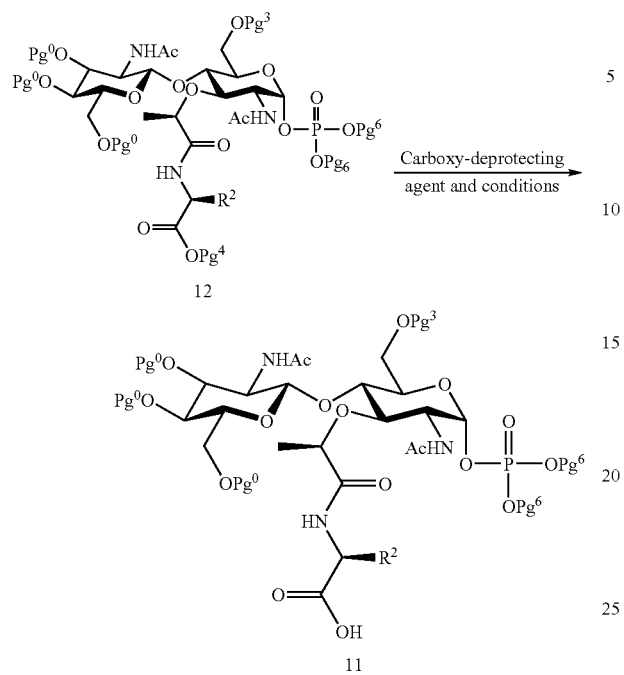

12

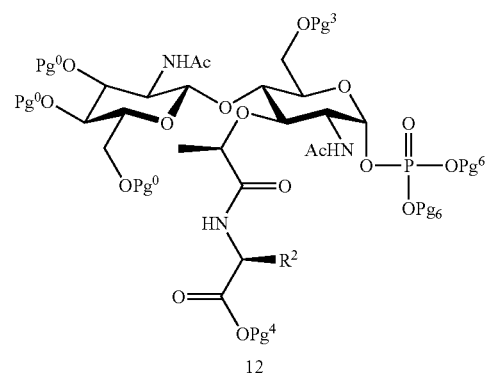

12

A particular compound of formula $L^2P(OPg^6)_2$ is $Et_2NP(OBn)_2$, or the like. Particular phosphitylation conditions encompass rapidly adding the lactone in anhydrous $CH_2Cl_2$, or the like to a vigorously stirred suspension of tetrazole, or the like and $Et_2NP(OBn)_2$, or the like in anhydrous $CH_2Cl_2$ under argon at about 25° C. A particular oxidizing agent is $H_2O_2$, or the like. Particular oxidizing conditions encompass dissolving the phosphate in THF, or the like and cooling to about −80° C. Then, $H_2O_2$, or the like, is added dropwise to the vigorously stirred solution. After the addition is complete, the ice bath is removed and the mixture allowed to warm to about room temperature over about 2 h. The phosphitylation/coupling sequence is described, for example, in Wong, C.-H, et al., *J. Am. Chem. Soc.* 115, 2260 (1993); Hitchcock, S. A., et al. *J. Am. Chem. Soc.* 120, 1916 (1998); and Walker, S., et al., *J. Am. Chem. Soc.* 120, 2484 (1998), all of which are incorporated herein by reference.

11 agent under appropriate conditions. The carboxy-deprotecting is carried out using an appropriate deprotecting agent that depends on the nature of the carboxy-protecting group, i.e., whether it is removable (labile) under acid, base, or hydrogenation conditions, and other reactive moieties in the compound undergoing deprotection, i.e., a deprotecting agent is chosen to carry out the deprotection without affecting the other reactive moieties unless a concomitant reaction is desired. A particular $Pg^4$ group is —$CH_2CH_2SO_2Ph$, or the like. A particular deprotecting agent is DBU, or the like. Particular conditions encompass dissolving compound 12 in $CH_2Cl_2$, or the like and adding DBU, or the like dropwise under an argon atmosphere, or the like.

A phospotriester of formula 12, wherein the variables are as described herein, may be prepared by (1) coupling a lactol of formula 13, wherein the variables are as described herein, with a compound of formula $L^2P(OPg^6)_2$, wherein $L^2$ is a leaving group and the other variables are as described herein, under appropriate phosphitylation conditions and (2) oxidizing the resulting phosphite to a phosphate in the presence of an oxidizing agent under appropriate oxidizing conditions.

A lactol of formula 13, wherein the variables are as described herein, may be prepared by removing the $Pg^5$ group of an anomeric benzyl ether of formula 14, wherein the variables are as described herein, in the presence of a hydroxy-deprotecting agent under appropriate conditions.

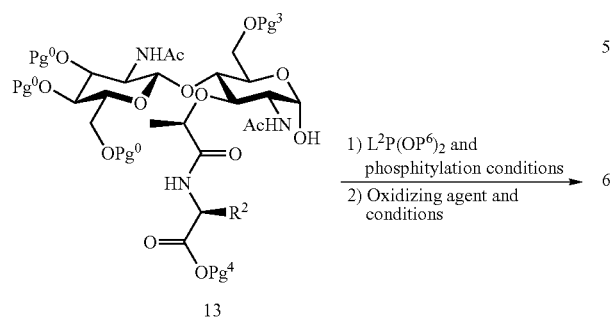

13

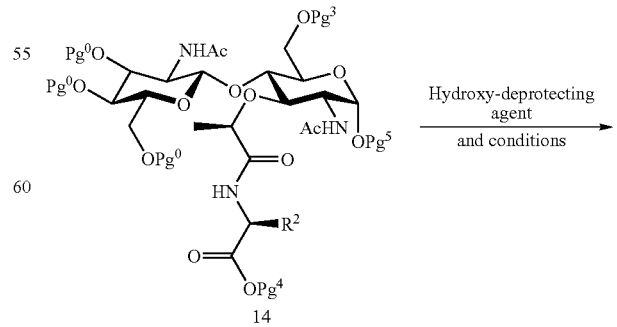

14

-continued

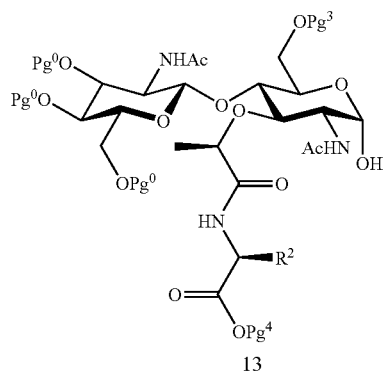

13

A particular Pg⁵ group is benzyl, or the like. A particular hydroxy-deprotecting agent is $H_2/(Pd/C)$, or the like. Particular conditions encompass dissolving the benzyl ether in HCl/acetic acid, or the like, and adding the resulting solution to a suspension of about 10% Pd/C, or the like in HCl/acetic acid, or the like. The reaction mixture is stirred under about an atmosphere of hydrogen at about 25° C. for 1.5 h.

General Preparation of Lipid XI

Lipid II, wherein A is as described herein, may be prepared by removing the $Pg^0$, $Pg^3$, $Pg^7$ and $Pg^8$ groups of a compound of formula 2a, wherein the variables are as described herein, in the presence of a

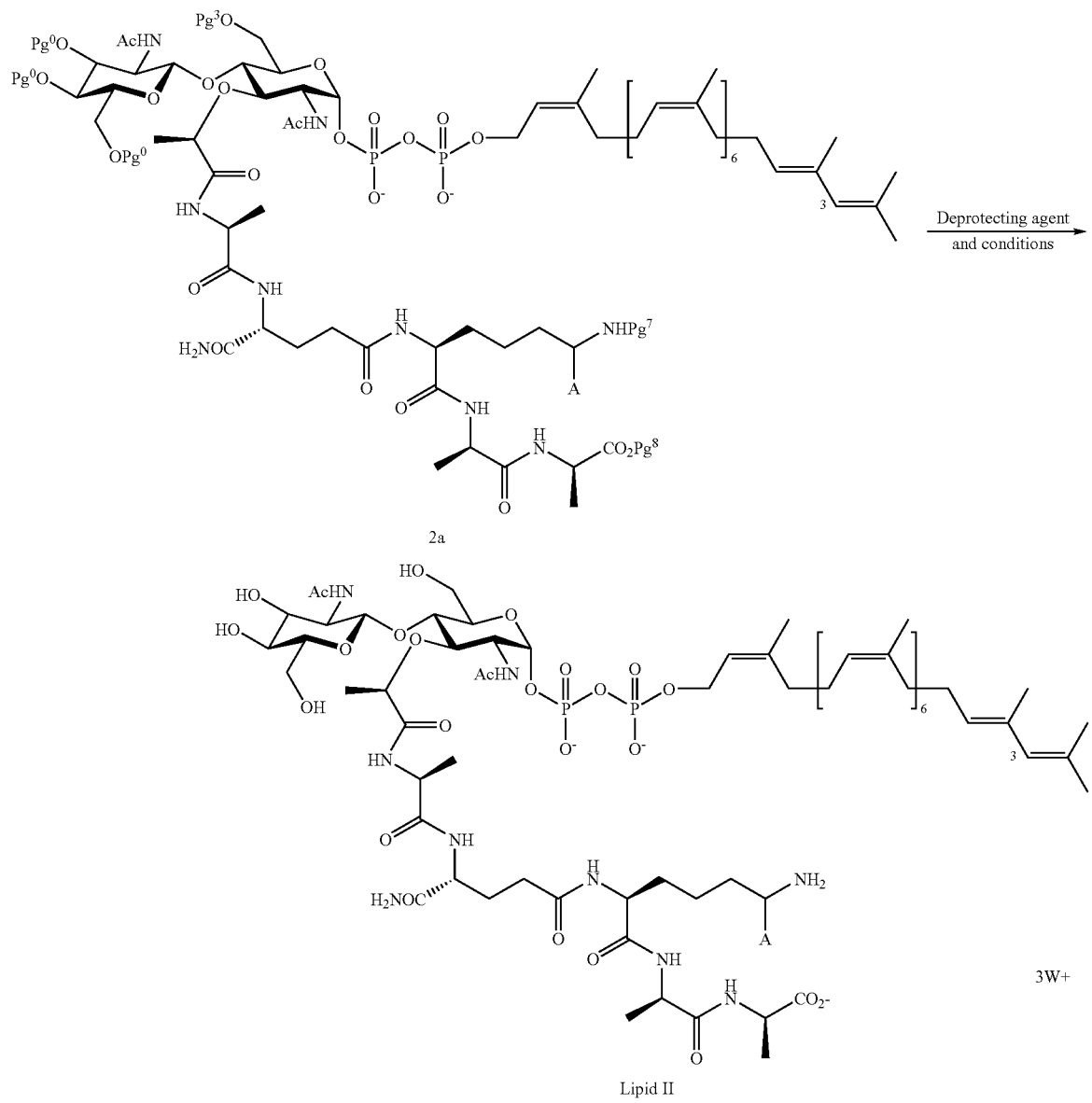

deprotecting agent under appropriate conditions. Particular Pg⁰ and Pg³ groups are acetyl, or the like. A particular Pg⁷ group is trifluoroacetyl, or the like. A particular Pg⁸ group is methyl, or the like. A particular deprotecting agent is aqueous sodium hydroxide, or the like. Particular conditions encompass carrying out the deprotection in about a 1:1 solution of 1,4-dioxane:water, or the like while stirring for about 2 h. Care must be exercised when exposing the pentapeptide to hydroxide ion mediated deprotection conditions for substantially longer periods of time since the base-catalyzed rearrangement of iso-glutamine to glutamine in peptidoglycan-related structures has been observed. (see, e.g., Keglevic, D. and A. E. Derome, *Carbohydrate Res.,* 186, 63 (1989); and Keglevic, D. and J. Kidric, *J. Carbohydrate Res.,* 11, 119 (1992), incorporated herein by reference).

A compound of formula 2a, wherein the variables are as described herein, may be prepared by treating an activated phosphate of formula 4a, wherein the variables are as described herein, with an undecaprenyl monophospate of formula 3a, wherein B² is as described herein, under appropriate coupling conditions.

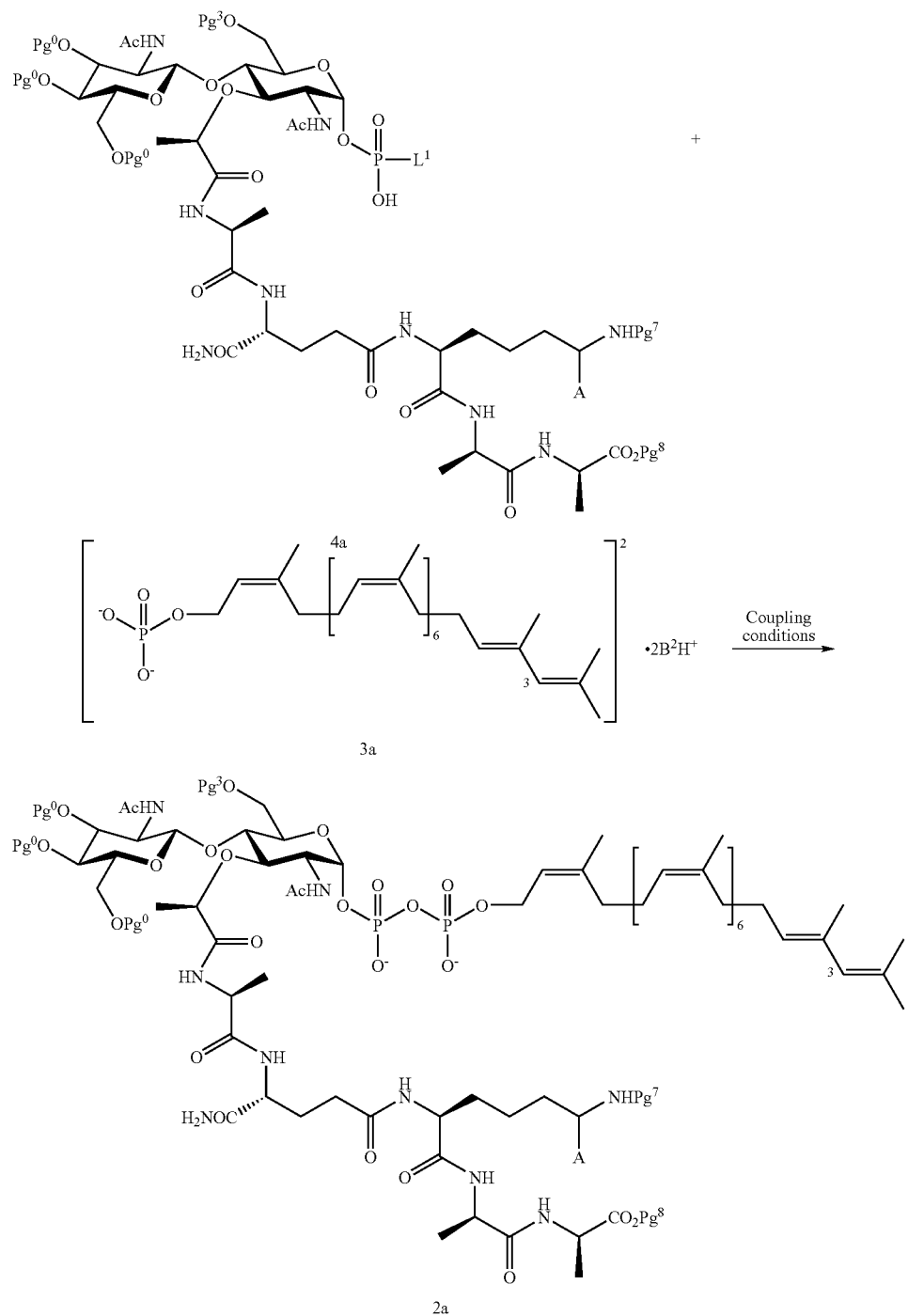

A particular -$L^1$ is imidazolyl, or the like. A particular compound of formula 3a is undecaprenyl monophosphate (bis-$NH_4^+$ salt). Particular conditions encompass exposing the activated phosphate to undecaprenyl monophosphate (bis-$NH_4^+$ salt) in the presence of 1H-tetrazole, or the like, over about 4 days in DMF/THF, or the like, under an argon atmosphere, or the like.

A compound of formula 4a, wherein the variables are as described herein, may be prepared by coupling a compound of formula 6a, wherein the variables are as described herein, with an activating agent of formula 5 under appropriate conditions.

CDI, or the like. A particular base counter ion, $BH^+$, is $C_5H_5NH^+$, or the like. Particular conditions encompass carrying out the reaction in anhydrous DMF/THF, or the like, for about 2 h. Electrophilic activation of the anomeric phosphate by conversion to the corresponding phosphorimidazolate derivative is described in Fang, X., et al., *Bioorg. Med. Chem. Lett.*, 5, 2701 (1995).

A compound of formula 6a, wherein the variables are as described herein, may be prepared by (1) removing the $Pg^6$ groups of a compound of compound of formula 7a, wherein the variables are as described herein, in the presence of a

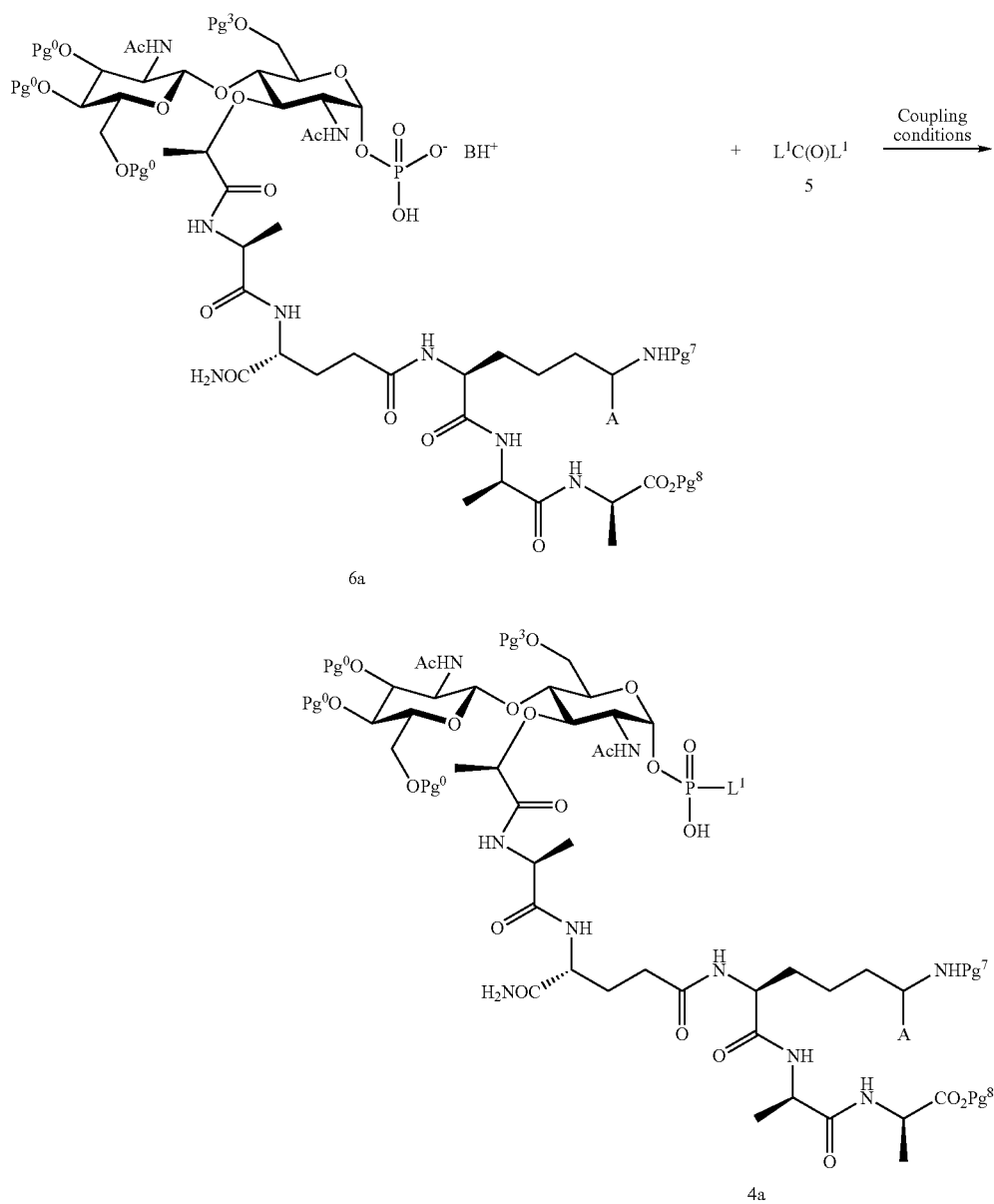

The coupling reaction initially forms a phosphate diester intermediate, which gives off $CO_2$ to yield the activated phosphate of formula 4a. A particular activating agent is hydrogenation agent under appropriate conditions, and (2) treating the resulting compound with a base of formula B to form a phosphate salt.

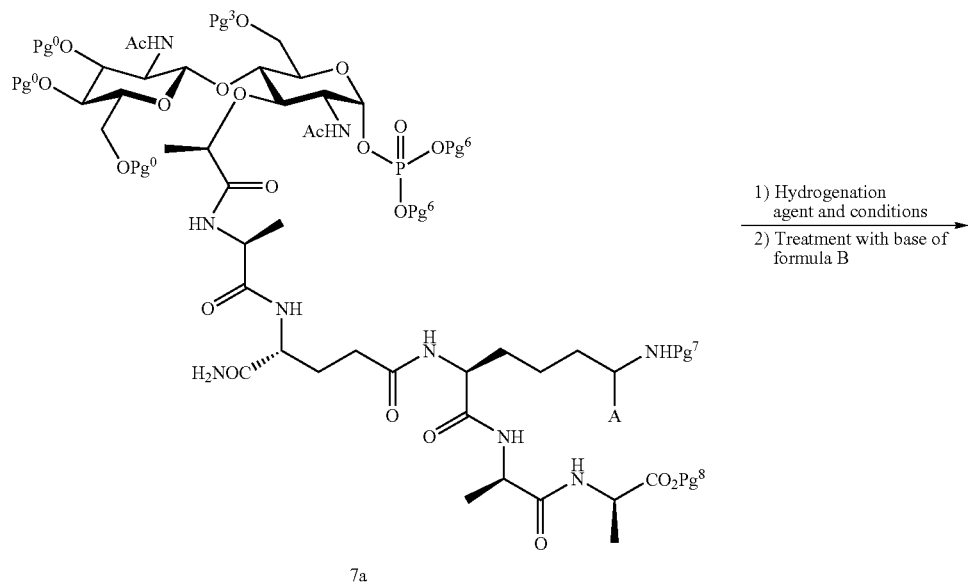

7a

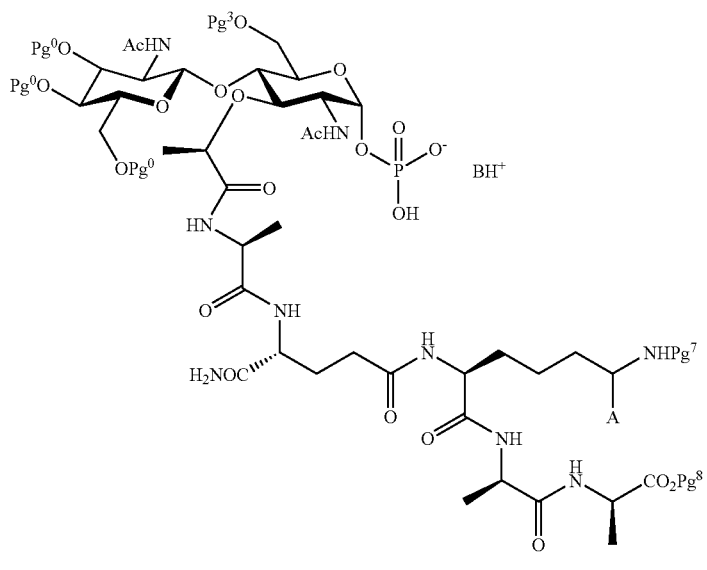

6a

A particular Pg⁶ group is benzyl, or the like. A particular hydrogenation agent is Pd/C, or the like. Particular hydrogenation condition encompasses adding the compound of formula 7a to a suspension of about 10% Pd/C, or the like, in alcohol (preferably methanol), or the like, cooled in an ice bath to aid in degassing the solution. The solution is then warmed to about room temperature and hydrogenated at atmospheric pressure for about 1.5 h. A particular base of formula B is pyridine, or the like.

A compound of formula 7a, wherein the variables are as described herein, may be prepared by coupling an activated ester of formula 9a, wherein the variables are as described herein, with a peptide of formula 8a, wherein the variables are as described herein, under appropriate conditions.

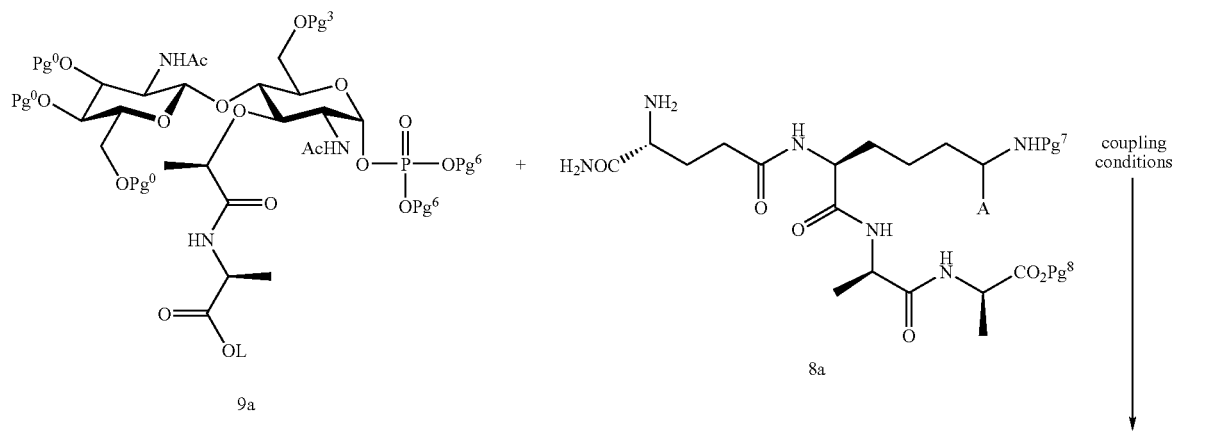

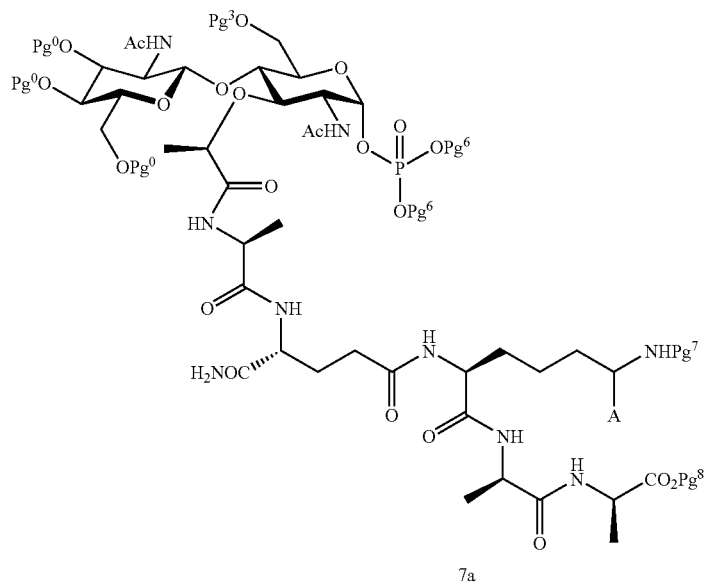

A particular —OL group is N-oxysuccinimide, or the like. Particular conditions encompass dissolving the compounds of formula 8a and 9a along with iPr$_2$NEt, or the like, in DMF, or the like, and stirring at about room temperature under argon, or the like for about 18 h. There is no evidence for the epimerization of the L-Ala α-stereocenter during the course of the carboxyl activation-peptide coupling sequence.

A compound of formula 8a, wherein the variables are as described herein, is prepared via conventional peptide synthetic methods known in the art.

General Preparation of the NAG-NAM Disaccharide Starting Material

A compound of formula 14, wherein the variables are as described herein, may be prepared by exchanging the Pg$^2$ group of a compound of formula 15, wherein the variables are as described herein, with an acetyl group in the presence of

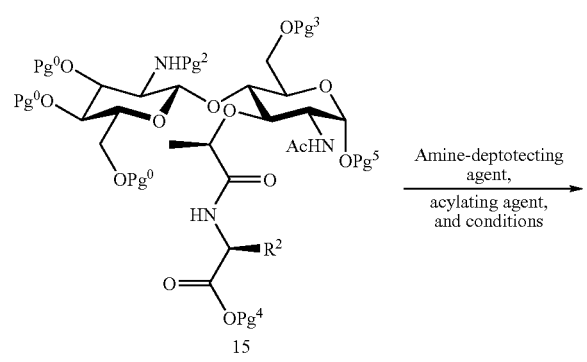

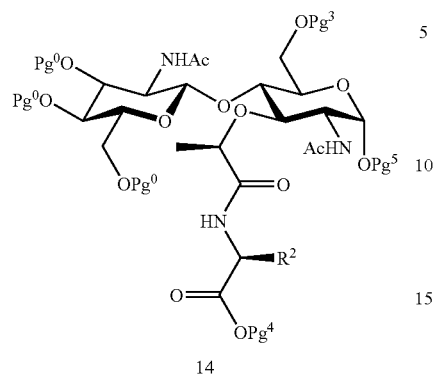

14

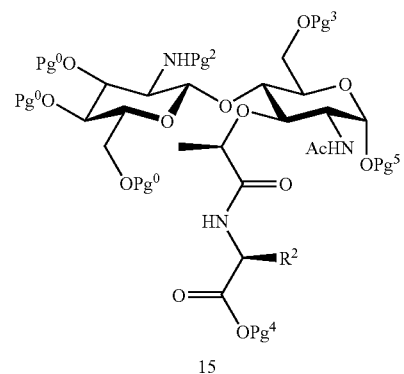

15 an amine-deprotecting agent and an acylating agent under the appropriate conditions. The amine-deprotecting is carried out using an appropriate deprotecting agent that depends on the nature of the amine-protecting group, i.e., whether it is removable (labile) under acid, base, or hydrogenation conditions, and other reactive moieties in the compound undergoing deprotection, i.e., a deprotecting agent is chosen to carry out the deprotection without affecting the other reactive moieties unless a concomitant reaction is desired. A particular amine-protecting group is 2,2,2-trichloroethoxycarbonyl, or the like. A particular deprotecting agent is Zn dust, or the like, in the presence of a proton source (e.g., acetic acid), or the like. A particular acylating agent is acetic anhydride, or the like. Particular conditions include adding Zn dust, or the like, and a 3:2:1 mixture of THF:$Ac_2O$:AcOH to a solution of the compound of formula 8 in about a 2:1 mixture of $Ac_2O$:AcOH, or the like.

A compound of formula 15, wherein the variables are as described herein, may be prepared by exchanging the $Pg^1$ group of a compound of formula 16, wherein the variables are as described herein, with a $Pg^3$ group in the presence of a

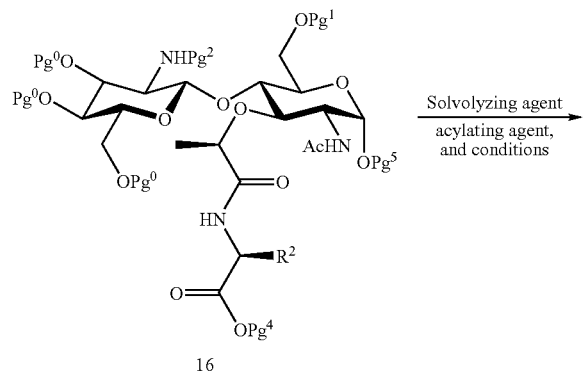

16 solvolyzing agent and acylating agent under appropriate conditions. The solvolysis is carried out using an appropriate solvolyzing agent that depends on the nature of the hydroxy-protecting group, i.e., a solvolyzing agent is chosen to carry out the solvolysis without affecting the other reactive moieties unless a concomitant reaction is desired. A particular hydroxy-protecting group is benzyl, or the like. A particular solvolyzing agent is $ZnCl_2$, or the like. A particular acylating agent is acetic anhydride, or the like. Particular conditions include carrying out the solvolysis/acylation in about a 2:1 mixture of $Ac_2O$:AcOH, or the like.

Synthesis of a compound of formula 16, the central disaccharide core, in orthogonally protected form presents a significant synthetic challenge. For example, identification of a protective scheme having triple orthogonality is highly desirable to accomplish selective unmasking of the three types of pendant hydroxyl groups (i.e., anomeric OH, peripheral OH, and carboxyl OH). In addition, the stereoselective construction of the β-[1,4] glycosidic linkage is expected to be difficult irrespective of the method used to generate a reactive glycosyl cation donor. For example, with respect to the glycosyl cation, each of the following inherent properties contribute to a loss of reactivity of the glycosyl cation acceptor: (i) the intrinsic lack of nucleophilicity of the C(4)-hydroxyl group of glucopyranose-based acceptors, (ii) additional steric crowding around the C(4)-hydroxyl of muramic acid-based acceptors, and (iii) additional electronic deactivation of 2-deoxy-2-acylaminoglucopyranose acceptors relative to their glucopyranose-based counterparts. With respect to the glycosyl cation donor, an activation method with a predisposition toward formation of a β-[1,4] glycosidic linkage is needed. The reaction conditions for glycosyl cation generation also needs to be compatible with functionality resident in both the donor and acceptor.

A compound of formula 16, wherein the variables are as described herein, may be prepared by coupling a muramylamide compound of formula 17, wherein $A^1$ is Br or Cl (preferably Br) and the other variables are as described herein, with a

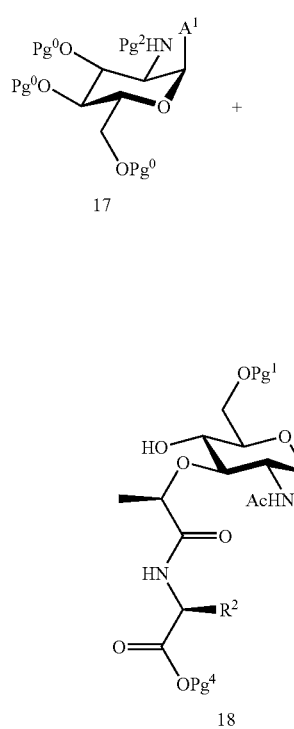

17

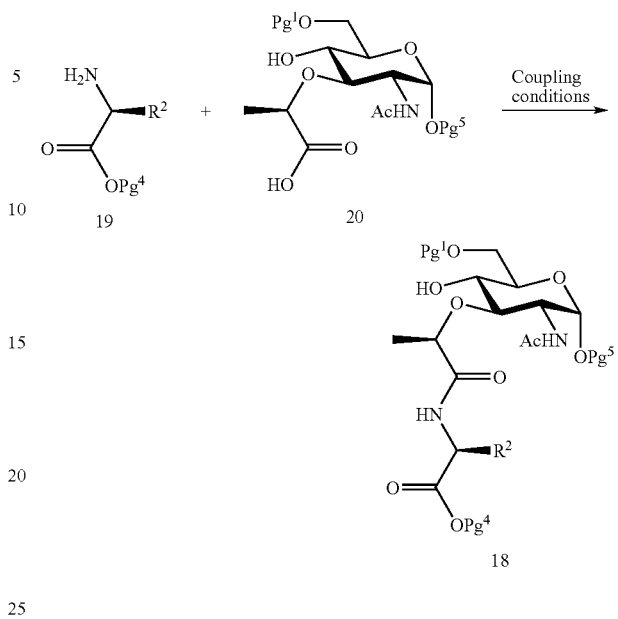

19   20

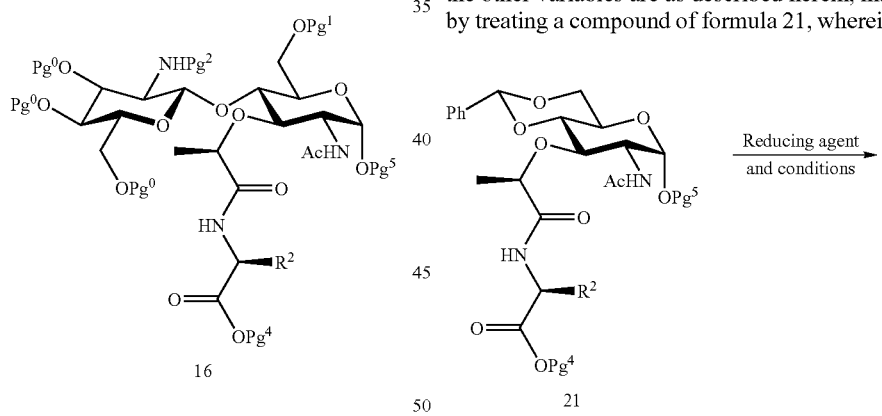

16   21

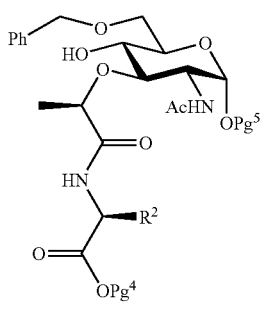

18a glucopyranosyl compound of formula 17, wherein the variables are as described herein, under appropriate conditions. Particular conditions include carrying out the coupling reaction under scrupulously anhydrous Konigs-Knorr conditions (e.g., in a silver triflate/dichloromethane solution including molecular sieves), or the like.

A compound of formula 17 is prepared according to the procedures described in Imoto, M., Bull. *Chem. Soc. Jpn.*, 60, 2205 (1987).

A compound of formula 18, wherein the variables are as described herein, may be prepared by coupling an acid of formula 20, wherein the variables are as described herein, with a protected amino acid/peptide compound of formula 19, wherein the variables are described herein, under appropriate conditions. Particular conditions encompass carrying out the coupling reaction in a solution of NMM, or the like, and 2-chloro-4,6-dimethoxy-1,3,5-triazine, or the like, in $CH_2Cl_2$, or the like, wherein the compound of formula 19 is added as the tosylate salt, or the like.

A compound of formula 18a, wherein $Pg^1$ is benzyl and the other variables are as described herein, may be prepared by treating a compound of formula 21, wherein the variables are as defined herein, with a reducing agent under appropriate conditions. A particular reducing agent is triethylsilane, or the like. Particular conditions include carrying out the reduction in $CH_2Cl_2$ or the like, and TFA, or the like, at about 0° C. This reaction provides an efficient means for regioselective introduction of the benzyl protection/activation at C(6)OH of the muramic acid derivative.

It is known that when an ester derivative of a compound of formula 21 is treated with trifluoroacetic acid and triethylsilane as described in DeNinno, M. P., et al., *Tetrahedron Lett.*, 36, 669 (1995), only a small amount of the analogous compound of formula 18a is observed. The major product formed is a lactone, as shown in scheme I.

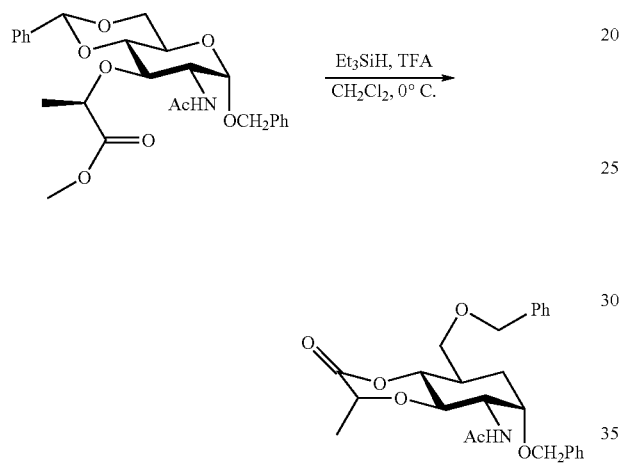

Scheme I

The acid-catalyzed lactonization proceeds at a rate competitive with the reductive ring opening, thus leading to the undesired lactone. In the present invention, however, introduction of an amide bond in place of the ester bond eliminates the conversion to the lactone, thus allowing the desired product (compound 18a) to be isolated in much higher yields.

A compound of formula 21, wherein the variables are as described herein, may be prepared by coupling an acid of formula 20a, wherein the variables are as described herein,

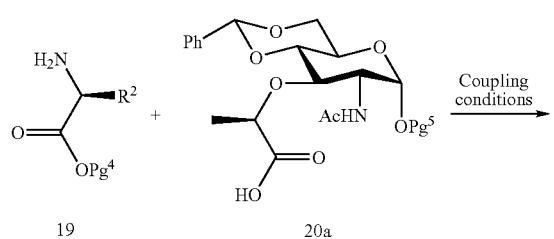

-continued

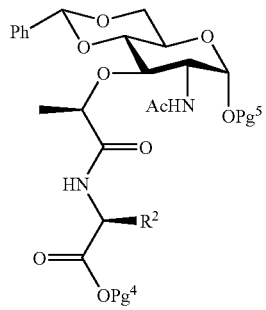

21 with a protected amino acid of formula 19, wherein the variables are described herein, under appropriate conditions. Particular conditions encompass carrying out the coupling reaction in a solution of NMM, or the like, and 2-chloro-4,6-dimethoxy-1,3,5-triazine, or the like, in $CH_2Cl_2$, or the like, wherein the protected amino acid is added as the tosylate salt, or the like.

General Experimental

Reactions are carried out with continuous stirring under a positive pressure of nitrogen except where noted. Reagents and solvents are purchased and used without further purification. TLC is performed using 0.25 mm silica gel 60 plates with a 254 nm fluorescent indicator from E. Merck. Plates are developed in a covered chamber and visualized by ultraviolet light or by treatment with 5% phosphomolybdic acid (or alternatively CAM) in ethanol followed by heating. Flash chromatography is carried out with silica gel 60, 230–400 mesh (0.040–0.063 mm particle size) purchased from EM Science. HPLC analyses and purifications are performed using Dynamax C8 columns with the specified solvent system and flow rate. NMR spectra are reported as chemical shifts in parts-per-million (ppm) downfield from a tetramethylsilane internal standard (0 ppm). $^1H$ NMR spectra are recorded in the solvent indicated on either a Bruker Avance spectrometer at 500.18 MHz, a Varian Mercury spectrometer at 400.21 MHz, or a GE QE-300 spectrometer at 300.15 MHz. $^{13}C$ NMR spectra are recorded in the solvents indicated on the previously mentioned spectrometers at 125.78 Mz, 100.15 MHz, and 75.48 MHz, respectively. IR spectra are recorded on a Nicolet 510P FT-IR spectrometer; electrospray ionization mass spectra (ESI-MS) are recorded on a Micromass Platform LCZ spectrometer. High resolution mass spectra are recorded on a Micromass QTOF mass spectrometer.

Preparation of the NAG-NAM Disaccharide
Starting Material
A synthetic process for preparing the NAG-NAM disaccharide starting material is outlined in Scheme II and exemplified below.
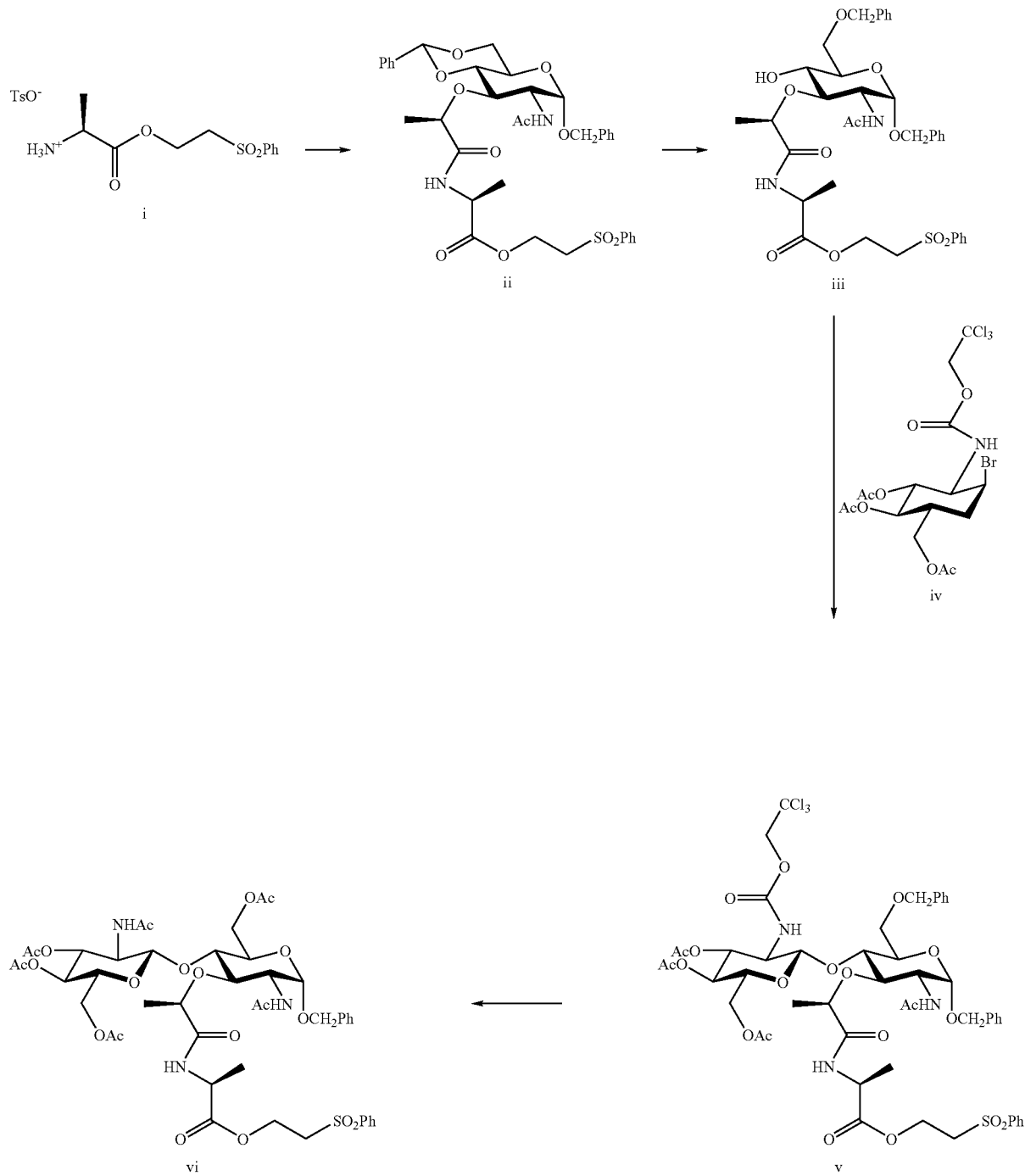
Scheme II I. Regioselective Installation of Benzyl Protection & Attachment of Peptide Linker:

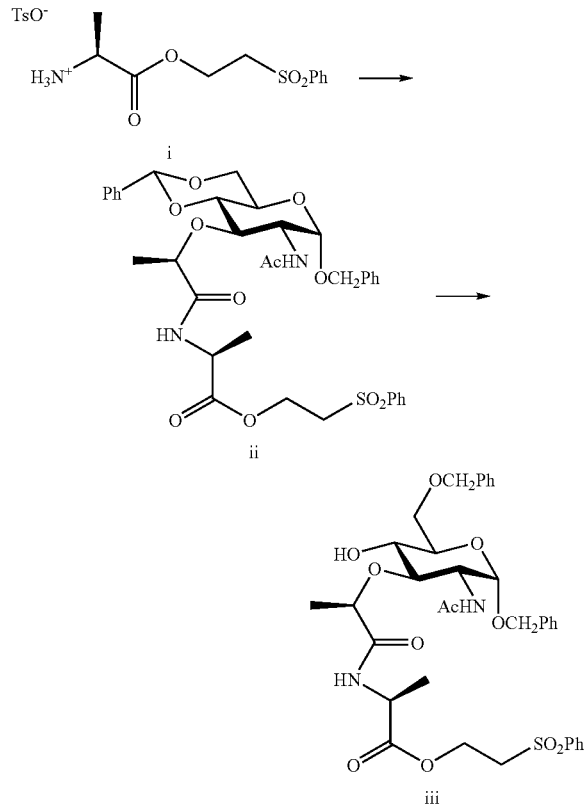

A mixture of (L)-alanine (15.0 g, 168 mmol), phenylsulfonyl ethanol (37.6 g, 202 mmol), and TsOH.H$_2$O (35.2 g, 185 mmol) in benzene (750 mL) is refluxed using a Dean-Stark apparatus. After 16 h, additional phenylsulfonyl ethanol (25 g, 135 mmol) and TsOH.H$_2$O (25 g, 134 mmol) is added along with benzene (180 mL), and the reaction mixture is refluxed overnight. Concentration in vacuo gives the product, compound i, in quantitative yield as a white solid.

Analytical (compound i): $^1$H NMR(DMSO-d$_6$, 300 MHz) δ 8.25(br s, impurities, TsOH), 7.94–7.88(m, 2H), 7.81–7.74 (q, J=6.2 Hz, 1H), 7.71–7.62(m, 2H), 7.49(d, J=8.1 Hz, 1H), 7.12(d, J=8.1 Hz, 1H), 5.39(br s, 2H), 4.52–4.44(m, 1H), 4.41–4.33(m, 1H), 3.90–3.82(m, 1H), 3.78(t, J=5.5 Hz, 2H), 3.67(t, J=6.2 Hz, 1H), 3.44(t, J=6.6 Hz, 1H), 2.29(s, 3H+impurities, TsOH), 1.20(d, J=7.3 Hz, 3H) $^{13}$C NMR (DMSO-d$_6$, 75 MHz) δ 169.5, 145.5, 139.3, 137.7, 134.1, 133.6, 129.5, 129.3, 128.0, 127.7, 127.6, 125.5, 58.9, 57.5, 54.9, 53.6, 47.7, 20.7, 15.2: MS(ESI) m/z 258.1 (100%, M-TsOH—H); IR KBr ν$_{max}$ 3424(br), 2927(br), 1745(m), 1309(m), 1224(m), 1195(m), 1147(s), 1124(m), 1087(m), 1007(m) cm$^{-1}$; Anal. Calcd for C$_{18}$H$_{25}$NO$_4$S: C, 50.10; H, 5.84; N, 3.25; S, 14.86. Found: C, 48.49; H, 5.31; N, 2.56; S, 14.72.

To a slurry of benzyl N-acetyl-4,6-benzylidine muramic acid (20.0 g, 42.5 mmol) in CH$_2$Cl$_2$ (300 mL) at 0° C. is added N-methylmorpholine (NMM) (4.67 mL, 42.5 mmol) and 2-chloro-4,6-dimethoxy-1,3,5-triazine (8.94 g, 51.0 mmol). After stirring for 45 min at 0° C., CH$_2$Cl$_2$ (300 mL) followed by NMM (9.34 mL, 83.0 mmol) and L-alanine (phenylsulfonylethyl ester, tosylate salt) (15.4 g, 51.0 mmol) (i.e., compound i) are added to the above reaction mixture. The resulting solution is slowly warmed to room temperature and stirred for 3 days. The reaction mixture is then filtered. The filtrate is washed first with 1N HCl then with brine, and dried (MgSO$_4$). The filtrate is then concentrated under reduced pressure, evaporated with toluene(x2), and vacuum dried overnight to afford the product, compound ii, (23.5 g, 95%) as a white solid.

Analytical (compound ii): $^1$H NMR (CDCl$_3$, 400 MHz) δ 7.44(d, J=3.0 Hz, 2H), 7.35(m, 8H), 6.95(d, J=6 Hz, 1H), 6.15(d, J=6.0 Hz, 1H), 5.85(m, 1H), 5.47(s, 1H), 5.21(dd, J=3.0, 12.0 Hz, 1H), 5.30(dd, J=3.0, 15.0 Hz, 1H), 4.90(d, J=3.0 Hz, 1H), 4.72(d, J=12.0 Hz, 1H), 4.60(m, 2H), 4.42(m, 2H), 4.30–4.20(m, 2H), 4.15(q, J=3.0 Hz, 1H), 4.00(q, J=3.0 Hz, 1H), 3.82(m, 1H), 3.75(d, J=9.0 Hz, 1H), 3.65(m, 1H), 1.93(s, 3H), 1.43(d, J=3.0, 9.0 Hz, 3H), 1.38(d, J=3.0, 9.0 Hz, 3H); $^{13}$C NMR (CDCl$_3$, 75 MHz) δ 173.2, 172.2, 170.6, 131.6, 129.0, 128.9, 128.4, 128.3, 125.9, 101.4, 97.5, 81.7, 78.3, 76.6, 75.6, 75.1, 70.1, 68.9, 65.8, 64.1, 63.2, 55.3, 53.2, 48.1, 23.0, 17.4, 17.8. MS (ESI) m/z 583.2 (86%, M+H), 581.3(100%, M−H); IR ν$_{max}$ (CHCl$_3$) 3010(m), 1740(m), 1681(s), 1616(m), 1569(s), 1523(m), 1470(m), 1377(s), 1333(m), 1119(m), 1090(m) cm$^{-1}$; Anal. Calcd for C$_{31}$H$_{38}$N$_2$O$_9$: C, 63.90; H, 6.57; N, 4.81. Found: C, 63.78; H, 6.55; N, 4.89.

Triethylsilane (16.4 mL, 103 mmol) is added to a solution of compound ii (12.0 g, 20.6 mmol) in CH$_2$Cl$_2$ (150 mL) at 0° C., followed by dropwise addition of TFA (8.1 mL, 103 mmol). The mixture is allowed to stir for 5 h, after which an additional 3 equivalents of TFA (5.0 mL) is added dropwise, and stirred at 0° C. overnight. Upon completion of the reaction, as evidenced by TLC (EtOAc), the reaction mixture is diluted with CH$_2$Cl$_2$, then NaHCO$_3$ is added slowly to neutralize the TFA. The aqueous layer is extracted with CH$_2$Cl$_2$. The organic layer is washed with brine (x2), then dried (MgSO$_4$), and concentrated in vacuo. Purification by prep-LC (eluting with 70:30 EtOAc:hexane to EtOAc), followed by recrystallization from CH$_2$Cl$_2$ and isopropyl ether gives the product, compound iii, (7.4 g, 61%) as a white solid.

Analytical (compound iii): $^1$H NMR (CDCl$_3$, 300 MHz) δ 7.38–7.26(m, 10H), 6.99 d, J=7.3 Hz, 1H), 6.16(d, J=8.8 Hz, 1H), 5.94–5.81(m, 1H), 5.30(dd, J=1.1, 17.2 Hz, 1H), 5.22(dd, J=1.1, 10.6 Hz, 1H), 4.92(d, J=3.7 Hz, 2H), 4.68(t, J=11.7 Hz, 1H), 4.59(d, J=7.7 Hz, 4H), 4.49(q, J=6.2 Hz, 1H), 4.46(dd, J=2.2, 11.7 Hz, 2H), 4.21(dq, J=3.7, 9.9 Hz, 1H), 4.17(q, J=7.0 Hz, 1H), 3.83–3.75(m, 1H), 3.71(t, J=5.1 Hz, 1H), 3.68–3.65(m, 1H), 3.54(t, J=10.2 Hz, 1H), 1.89(s, 3H), 1.44(d, J=7.0 Hz, 3H), 1.40(d, J=7.0 Hz, 3H); $^{13}$C NMR(CDCl$_3$, 75 MHz) δ 173.0, 172.3, 170.3, 167.7, 137.8, 137.1, 131.7, 128.6, 128.5, 128.1, 127.8, 127.7, 118.5, 97.1, 80.5, 77.7, 73.7, 71.6, 70.5, 70.2, 69.8, 65.8, 55.1, 52.5, 48.0, 24.5, 23.3, 19.2, 17.7; MS(ESI) m/z 585.2 (100%, M+H), 583.2 (100%, M−H); IR ν$_{max}$(CHCl$_3$) 3433(m), 3010(m), 1741(m), 1677(s), 1522(m), 1454(m), 1124(m), 1058(m) cm$^{-1}$; Anal. Calcd for C$_{31}$H$_{40}$N$_2$O$_9$: C, 63.68; H, 6.90; N, 4.79; Found: C, 63.67; H, 6.58; N, 4.83.

II. Glycosidation

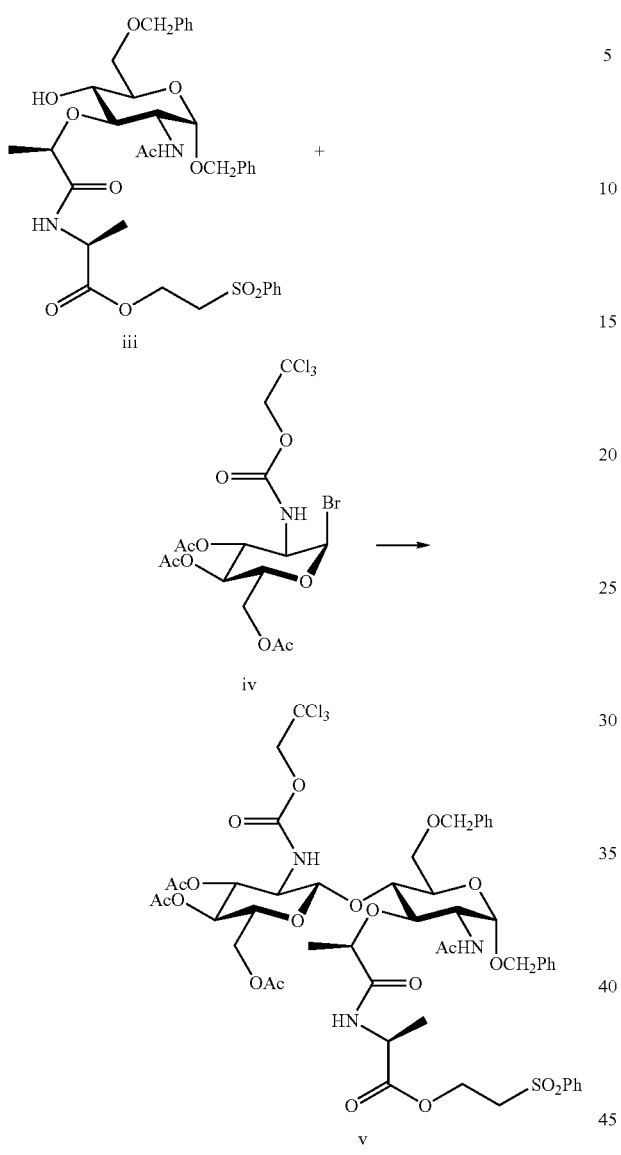

Compound iv is prepared using the procedures described in Imoto, M., *Bull. Chem. Soc. Jpn.*, 60, 2205 (1987).

To a solution of compound iii (4.59 g, 6.43 mmol) in $CH_2Cl_2$ (30 mL) are added 4 Å molecular sieves (10 g) and silver triflate (5.12 g, 20.0 mmol). To this mixture is added a solution of freshly prepared compound iv (10.8 g, 20.0 mmol) in $CH_2Cl_2$ (9.5 mL) in four portions over a 1 h period. Each of the starting materials is dried prior to use, and the reaction is performed under controlled anhydrous conditions. After stirring at room temperature for 24 h, the reaction mixture is filtered through Celite and washed with $CH_2Cl_2$. The organic layer is washed with $NaHCO_3$, brine, dried ($Na_2SO_4$), and concentrated in vacuo. Purification by column chromatography on silica (Flash Elute system) utilizing a solvent gradient of 50% hexane in EtOAc, 15% hexane in EtOAc, EtOAc, and 5% MeOH in EtOAc yields the product, compound v, (5.73 g, 76%) as a white solid, along with unreacted starting material, compound iii, (630 mg, 14%).

Analytical (compound v): $^1H$ NMR($CDCl_3$, 300 MHz) 67.91(d, J=7.0 Hz, 2H), 7.66(t, J=7.3 Hz, 1H), 7.58–7.50(m, 4H), 7.45(t, J=7.3 Hz, 2H), 7.33–7.26(m, 6H), 6.83(d, J=7.3 Hz, 1H), 6.52(d, J=7.0 Hz, 1H), 5.09(d, J=2.9 Hz, 1H), 4.97(t, J=9.5 Hz, 1H), 4.87(d, J=12.1 Hz, 1H), 4.79–4.73(m, 2H), 4.60(dd, J=7.3, 12.1 Hz, 2H), 4.53–4.29(m, 5H), 4.26–4.04(m, 7H), 4.00–3.88(m, 2H), 3.70–3.50(m, 4H), 3.42(t, J=10.6 Hz, 4H), 2.03(s, 3H), 1.98(s, 6H), 1.89(s, 3H), 1.34(d, J=6.6 Hz, 3H), 1.24(d, J=7.3 Hz, 3H); $^{13}C$ NMR ($CDCl_3$, 75 MHz) 6173.4, 171.8, 170.6, 170.3, 169.4, 154.1, 137.3, 134.0, 129.4, 129.1, 128.5, 128.1, 100.0, 97.1, 96.9, 77.4, 77.0, 76.6, 75.7, 74.5, 73.8, 72.2, 71.2, 70.4, 70.3, 68.3, 67.2, 61.5, 58.1, 26.2, 54.9, 53.6, 47.7, 23.2, 20.6, 18.3, 17.5; MS (FAB) m/z 1176.3 (73%, M+H), (ESI) m/z 1174.5 (62%, M–H) IR (KBr) $\nu_{max}$ 3385(br), 3067(w), 2939(w), 1753(s), 1669 m), 1537(m), 1233(s), 1145(m), 1045(s) $cm^{-1}$; UV-vis (95% EtOH) $\lambda_{max}$ 264 (1223.11) nm; Anal. Calcd for $C_{51}H_{64}Cl_3N_3O_2OS$: C, 52.02; H, 5.48; N, 3.57; S, 2.72; Cl, 9.03. Found: C, 51.72; H, 5.40; N, 3.64; S, 2.72; Cl, 9.07.

III. Protective Group Interchange

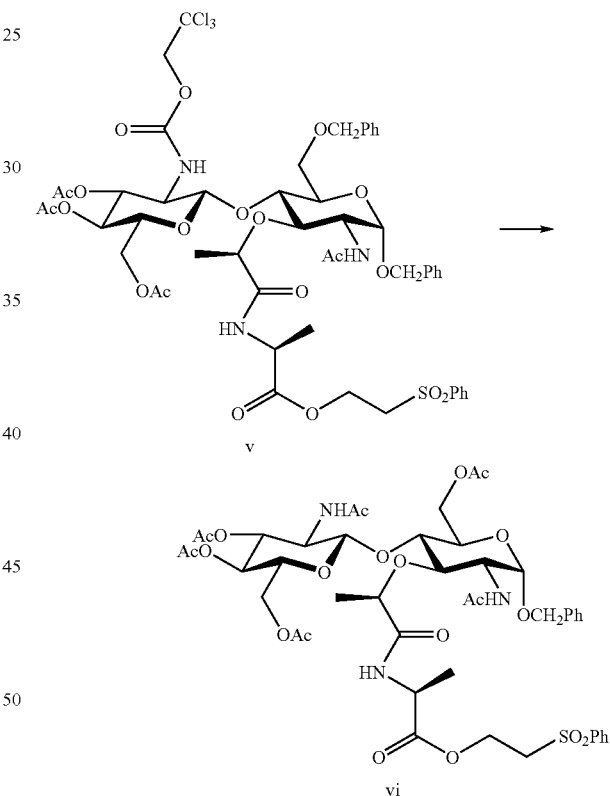

To a solution of compound v (1.9 g, 1.57 mmol) in $Ac_2O:AcOH$ (2:1, 11 mL) is added a solution of $ZnCl_2$ (2.1 g, 15.7 mmol) in $Ac_2O:AcOH$ (2:1, 5 mL) in one portion. Upon completion of the reaction (24 h) as judged by TLC (EtOAc), Troc is removed by adding Zn dust (4.1 g, 62.8 mmol) and a mixture of $THF:Ac_2O:AcOH$ (3:2:1, 25 mL) to the above reaction mixture and stirring until no starting material is evidenced by TLC (EtOAc). The reaction mixture is filtered through Celite, washed with EtOAc, and then concentrated under reduced pressure. The residue is repeatedly evaporated with toluene to remove any remaining $Ac_2O$ and AcOH, and then diluted with EtOAc. The organic layer is washed with NaHCO$_3$ (x2), H$_2$O (x2), and brine. The organic layer is then dried (Na$_2$SO$_4$) and concentrated in vacuo. Purification via column chromatography on silica (Flash Elute system) eluting with 2% MeOH in EtOAc affords the product, compound vi, (1.0 g, 67%) as a white solid.

Analytical (compound vi): $^1$H NMR (CDCl$_3$, 300 MHz) δ 7.89(d, J=7.0 Hz, 2H), 7.66(t, J=7.3 Hz, 1H), 7.56(t, J=7.7 Hz, 2H), 7.34–7.23(m, 6H), 7.16(d, J=7.7 Hz, 1H), 6.88(d, J=7.0 Hz, 1H), 6.12(d, J=9.5 Hz, 1H), 5.12–5.07(m, 3H), 4.56 (dd, J=12.1, 40.0 Hz, 2H), 4.45(d, J=9.0 Hz, 1H), 4.39(d, J=8.4 Hz, 1H), 4.35–4.23(m, 4H), 4.17(d, J=12.0 Hz, 2H), 4.09–3.95(m, 3H), 3.78(d, J=5.5 Hz, 2H), 3.60–3.48(m, 3H), 3.41–3.30(m, 2H), 2.12(s, 3H), 2.01(s, 3H), 2.00(s, 3H), 1.99(s, 3H), 1.94(s, 3H), 1.92(s, 3H), 1.38 (d, J=6.6 Hz, 3H), 1.28(d, J=7.3 Hz, 3H); $^{13}$C NMR(CDCl$_3$, 75 MHz) δ173.8, 171.9, 171.2, 170.9, 170.8, 170.6, 169.3, 139.2, 137.3, 134.1, 129.4, 128.9, 128.5, 128.1, 128.0, 127.8, 100.2, 96.9, 77.1, 76.6, 75.9, 75.6, 72.5, 71.8, 70.2, 69.5, 68.2, 62.3, 61.6, 58.0, 54.9, 54.6, 53.6, 47.8, 23.2, 23.1, 20.9, 20.6, 18.4, 17.3; MS (ESI) m/z 994.7 (100%, M–H); IR (KBr) ν$_{max}$ 3384(br), 3301(br), 3068(w), 2939(w), 1748(s), 1670(s), 1540(m), 1372(m), 1236(s), 1144(m), 1041(s) cm$^{-1}$; Anal. Calcd for C$_{45}$H$_{61}$N$_3$O$_{20}$S: C, 54.26; H, 6.17; N, 4.22; S, 3.22. Found: C, 53.96; H, 5.78; N, 4.17; S, 3.09.

Preparation of the Tetrapeptide Starting Material

I. Preparation of Cbz-D-iGln (compound ix)

Z-D-Glu(O-t-Bu)—OH ⟶
vii

Cbz-D-iGln(O$^t$Bu) ⟶ Cbz-D-iGln
viii              ix

A solution of Z-D-Glu(O-t-Bu)—OH (5.00 g, 14.82 mmol of compound vii), 1-(3-dimethylaminopropyl)-3-ethylcarbodiimide hydrochloride (2.85 g, 14.87 mmol), and N-hydroxysuccinimide (1.71 g, 14.86 mmol) in 1,4-dioxane (60 mL) and N,N-dimethylformamide (10 mL) is stirred for 6 h under N$_2$. Ammonium hydroxide (0.7 mL, 17.78 mmol) is added, then the solution is stirred 16 h, and concentrated in vacuo. The oil obtained is partitioned between ethyl acetate (200 mL) and brine (200 mL). The organic layer is dried over sodium sulfate, filtered, and concentrated in vacuo to a solid. The solid is chromatographed over flash silica gel (ethyl acetate:hexanes—1:1) to give Cbz-D-iGln(O$^t$Bu) (3.2 g, 64% yield of compound viii) as a white solid.

Analytical (compound viii): mp 134–135° C. IR(CHCl$_3$) 2985, 1717, 1695, 1155 cm$^{-1}$; $^1$H NMR(DMSO-d$_6$, 300 MHz) δ 7.35(s, 5H), 7.30(brs, 1H), 5.02(s, 2H), 3.94(m, 1H), 2.22(t, J=7.7 Hz, 2H), 1.86(m, 1H), 1.69(m, 1H), 1.38(s, 9H); MS (ESI) m/z 337 (80%, M+H); Anal. Calcd for C$_{17}$H$_{24}$N$_2$O$_5$: C, 60.70; H, 7.19; N, 8.33. Found C, 60.41; H, 7.15; N, 8.16.

Trifluoroacetic acid (25 mL) is added to a solution of Cbz-D-iGln(O$^t$Bu) (3.20 g, 9.52 mmol of compound viii) in methylene chloride (25 mL) and the mixture is stirred for 3 h under N$_2$. The solution is evaporated to give a white solid, filtered with the aid of ethyl ether, and dried in high vacuum to provide homogeneous Cbz-D-iGln (2.2 g, 82% yield of compound ix).

Analytical (compound ix): mp 174–176° C. IR (KBr) 3314, 1699, 1658, 1254 cm$^{-1}$; $^1$H NMR(DMSO-d$_6$, 300 MHz) δ 7.35(s, 5H), 7.31(s, 1H), 7.01(s, 1H), 5.02(s, 2H), 3.93(m, 1H), 2.25(t, J=8.0 Hz, 2H), 1.92(m, 1H), 1.73(m, 1H); MS (ESI) m/z 281 (100%, M+H); Anal. Calcd for C$_{13}$H$_{16}$N$_2$O$_5$·0.25H$_2$O; C, 54.83; H, 5.79; N, 9.84. Found C, 55.12; H, 5.53; N, 9.88.

II. Preparation of Nα-Boc-Nγ-(TFA)-L-Lys-D-Ala-D-Ala-OMe (Compound xvi)

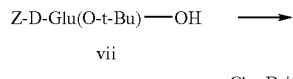
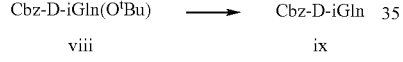
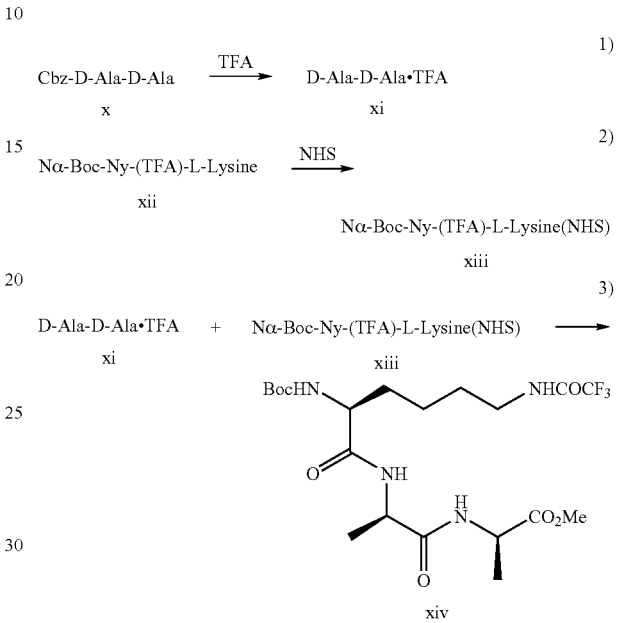

Cbz-D-Ala-D-Ala (1.20 g, 3.9 mM of compound x, available from Advanced Chem Tech., Louisville, Ky.) is dissolved in 10 mL methanol and added to a suspension of 500 mg Pd(OH)$_2$ in 15 mL methanol containing 0.3 mL TFA (3.9 mM). The mixture is stirred vigorously under one atmosphere of hydrogen (balloon pressure) for 2 h, filtered through talc, concentrated in vacuo, and the resulting compound xi (the TFA salt of D-Ala-D-Ala) stored under vacuum. Separately, Nα-Boc-Nγ-(TFA)-L-Lysine (1.40 g, 4 mM of compound xii, available from Bachem, Torrance, Calif.) and 830 mg DCC (4.0 mM) are dissolved in 15 mL dry THF and stirred at 0° C. for 3 h. N-hydroxysuccinimide (460 mg, 4.0 mM) is then added, after which the flask is allowed to warm to room temperature and stirred for an additional hour to give compound xiii, the NHS-activated ester of compound xii. The reaction mixture is then filtered directly into a flask containing compound xi, followed by the addition of 1.4 mL diisopropylethylamine (0.8 mM). After 30 minutes the reaction mixture is concentrated in vacuo, dissolved in ethyl acetate, washed with saturated aqueous NaHCO$_3$ and water, dried with MgSO$_4$ and then concentrated in vacuo to a white foam (1.4 g, 2.8 mM, 72% yield of compound xiv). The isolated material was used in the next step without further purification.

Analytical (compound xiv): $^1$H(CDCl$_3$): δ 1.37(d, 3H, J=7.5 Hz), 1.39(d, 3H, J=7.2 Hz), 1.4,(s, 9H), 1.75(m, 6H), 3.35(t, 2H, J=6.3 Hz), 3.75(s, 3H), 4.15(m, 1H), 4,48(m, 2H), 5.1(d, 1H), 6.67(d, 1H), 6.78(d, 1H). MS(FD$^+$): 499. EA calc. for C$_{20}$H$_{33}$F$_3$N$_4$O$_7$; C, 48.2; H, 6.7; N, 11.2. Found: C, 47.9; H, 6.5; N, 11.1.

III. Preparation of Compound xviii

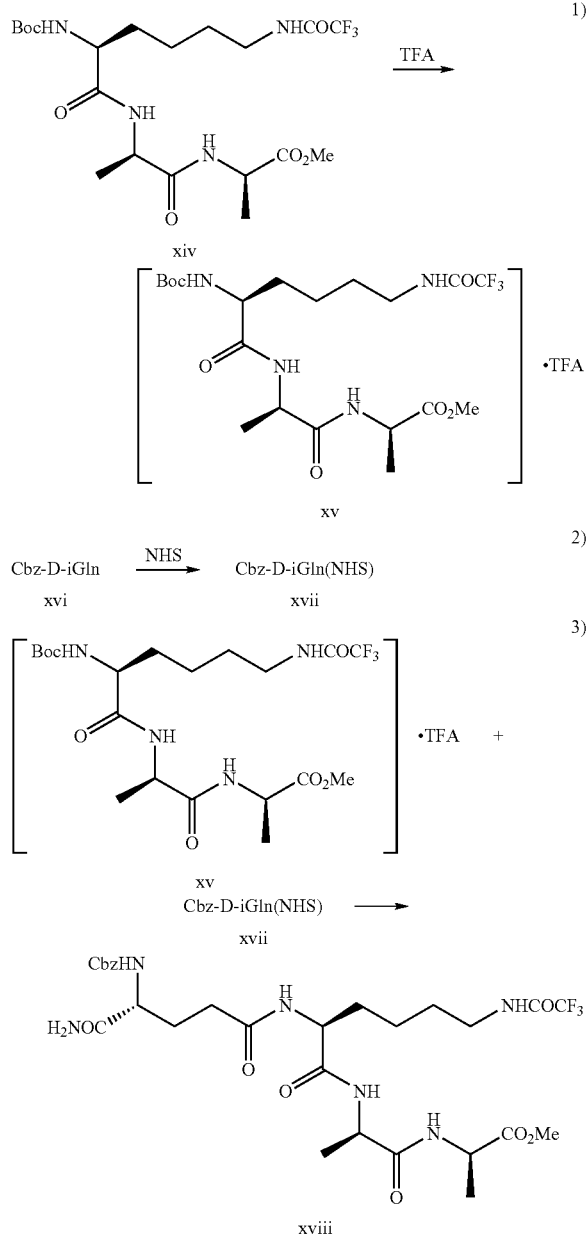

Trifluoroacetic acid (10 mL) is added to a solution of compound xiv (2.5 g, 5.0 mmol) in methylene chloride (10 mL) and the mixture is stirred for 2.5 h. The solution is concentrated in vacuo and dried under high vacuum to provide compound xv, the trifluoroacetate salt of compound xiv, as an oil. Separately, 1-(3-dimethylaminopropyl)-3-ethylcarbodiimide hydrochloride (1.88 g, 9.81 mmol) and N-hydroxysuccinimide (1.13 g, 9.81 mmol) are added to a solution of Cbz-D-iGln (2.20 g, 7.85 mmol of compound xvi) in N,N-dimethylformamide (25 mL). The mixture is stirred for 3 h, diluted to 100 mL with water and extracted with ethyl acetate (100 mL). The ethyl acetate solution is washed with saturated $NaHCO_3$ (100 mL), followed by brine (100 mL), and dried over sodium sulfate. The organic layer is evaporated to give Cbz-D-iGln(NHS) (1.96 g, 5.19 mmol of compound xvii), the NHS-activated ester of compound xvi, as a white solid. The solid thus obtained is added to a solution of the above-prepared compound xv (2.60 g, 5.07 mmol) in anhydrous DMF (25 mL), after which N,N-diisopropylethylamine (2.00 mL, 11.40 mmol) is added. The mixture is stirred for 72 h under $N_2$. Water (200 mL) is added and the mixture is stirred for 2 h. The resulting solid is filtered, washed with water (50 mL), and dried in high vacuum to give compound xviii (2.20 g, 66% yield).

Analytical (compound xviii): mp 237–240° C.; IR (KBr) 3302, 1699, 1669, 1630, 1184 cm$^{-1}$; $^1$H NMR(DMSO-d$_6$, 300 MHz) δ 9.36(t, J=5.0 Hz, 1H), 8.20(d, J=7.0 Hz, 1H), 8.13(d, J=7.7 Hz, 1H), 7.98(d, J=7.3 Hz, 1H), 7.35(m, 5H), 7.29(brs, 1H), 7.00(brs, 1H), 5.01(s, 2H), 4.25(m, 3H), 3.90(m, 1H), 3.60(s, 3H), 3.15(q, J=6.0, 12.0 Hz, 2H), 2.18(m, 2H), 1.85(m, 1H), 1.70(m, 1H), 1.55(m, 1H), 1.50 (m, 3H), 1.28(d, J=7.3 Hz, 3H), 1.27(m, 2H), 1.18(d, J=7.3 Hz, 3H); MS (ESI) m/z 661 (100%, M+H); Anal. Calcd for $C_{28}H_{39}N_6O_9F_3$: C, 50.91; H, 5.95; N, 12.72. Found C, 51.13; H, 6.21; N, 12.47.

IV. Preparation of Compound xix

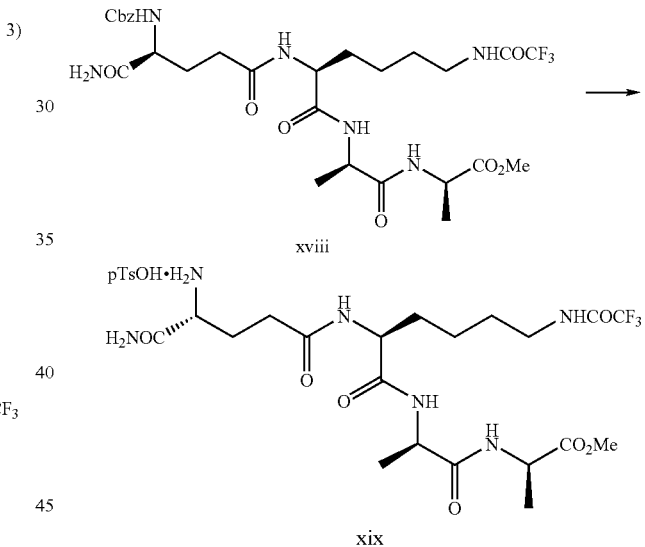

A mixture of compound xviii (2.15 g, 3.25 mmol), p-toluenesulfonic acid (662 mg, 3.25 mmol), and 5% Pd/C (500 mg) in methylene chloride:ethanol—1:1 (100 mL) is hydrogenated at room temp for 1.5 h at 60 psi. The catalyst is filtered and the solution is evaporated to a foam. The foam is dried in high vacuum to provide homogeneous compound xix (2.20 g, 97% yield).

Analytical (compound xix): IR(KBr) 3296, 1702, 1632, 1177 cm$^{-1}$; $^1$H NMR(DMSO-d$_6$, 300 MHz), δ 9.37(t, J=5.0 Hz, 1H), 8.23(d, J=6.6 Hz, 1H), 8.14(m, 2H), 8.04(brs, 3H), 7.79(s, 1H), 7.60(s, 1H), 7.46(d, J=8.0 Hz, 2H), 7.10(d, J=8.0 Hz, 2H), 4.25(m, 3H), 3.72(t, J=5.0 Hz, 1H), 3.61(s, 3H), 3.14(q, J=6.0, 12.0 Hz, 2H), 2.28(s, 3H), 2.25(m, 2H), 1.94(q, J=6.0, 12.0 Hz, 2H), 1.55(m, 4H), 1.28(d, J=7.3 Hz, 3H), 1.24(m, 2H), 1.18(d, J=7.09 Hz, 3H); MS (ESI) m/z 527 (100%, M+H). Anal. Calcd for $C_{27}H_{41}N_6O_{10}F_3S \cdot 0.5H_2O$: C, 45.83; H, 5.93; N, 11.87. Found C, 45.56; H, 5.73; N, 11.60.

Preparation of the Undecaprenyl Phosphate Diammonium Salt Starting Material (Compound xx)

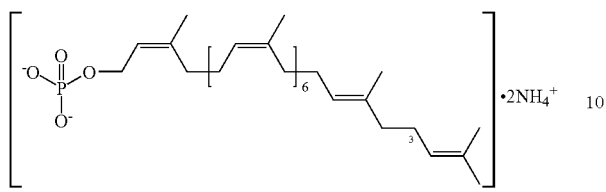

Compound xx, undecaprenol ($C_{55}$) monophosphate, diammonium salt, is purchased from Polish Academy of Sciences, Warsaw, Poland.

Preparation of Lipid II

A synthetic process for preparing lipid II, and key intermediates, from the starting material discussed above is outlined in Scheme III and exemplified below.

Scheme III

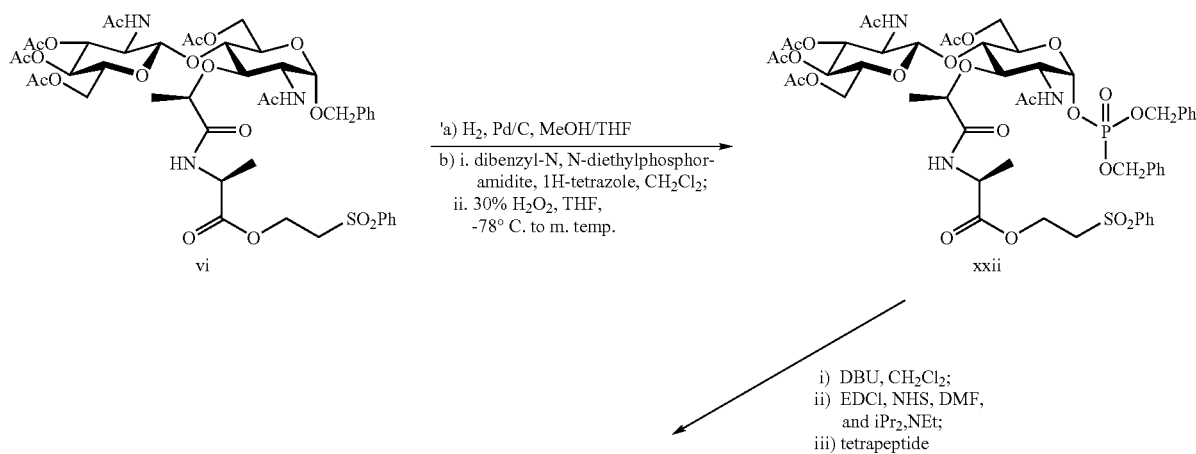

a) $H_2$, Pd/C, MeOH/THF
b) i. dibenzyl-N,N-diethylphosphoramidite, 1H-tetrazole, $CH_2Cl_2$;
   ii. 30% $H_2O_2$, THF, −78° C. to rm. temp.

i) DBU, $CH_2Cl_2$;
ii) EDCl, NHS, DMF, and $iPr_2NEt$;
iii) tetrapeptide

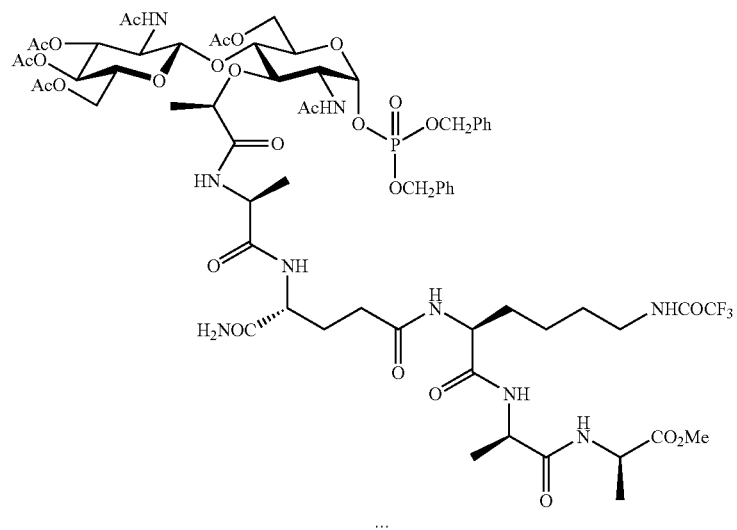

xxiii a) i. $H_2$, Pd/C, MeOH, then pyridine
b) i. CDI/DMF/THF;
   ii. undecaprenyl monophosphate (bis-$NH_4^+$ salt) and 1.1 eq. 1H-tetrazole;

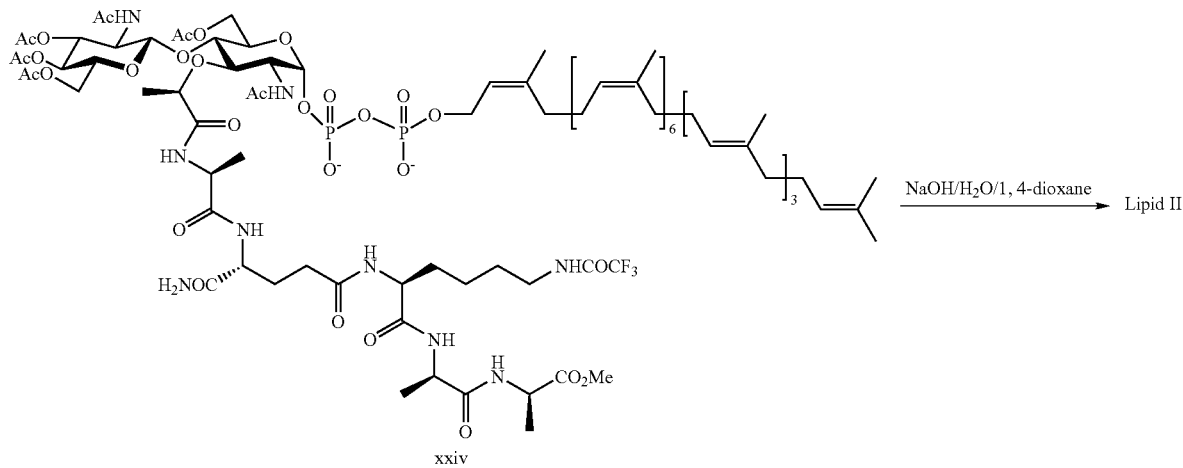

I. Preparation of the Lactol Intermediate (Compound XXI)

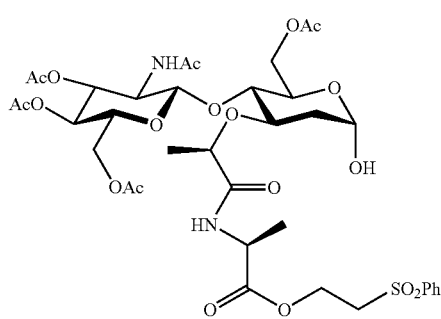

Compound vi (1.0 g, 1.0 mmol) is dissolved in 0.23 M HCl in acetic acid (5 mL) and added to a suspension of 10% Pd/C (0.50 g) in 0.23 M HCl in acetic acid (5 mL). The reaction mixture is stirred under an atmosphere of hydrogen (balloon, 15 psi) at 25° C. for 1.5 h. Analysis of the reaction mixture by thin layer chromatography (5% MeOH/CHCl$_3$) shows complete consumption of starting material. The reaction mixture is diluted with EtOAc and the catalyst is collected by filtration through a pad of Celite. The filtrate is carefully washed with aq. NaHCO$_3$ (x3) and water (x2). The aqueous extracts are combined and extracted with EtOAc. The combined organic layers are washed with brine, dried with Na$_2$SO$_4$, and concentrated in vacuo to afford the lactol product as a white solid (808 mg, 89% yield of compound xxi).

Analytical (compound xxi): $^1$H NMR(DMSO-d$_6$) δ 1.02 (d, J=6.84, 3H), 1.80(d, J=6.80, 3H), 1.70(s, 3H), 1.71(s, 3H), 1.84(s, 3H), 1.86(s, 3H), 1.89(s, 3H), 1.98(s, 3H), 3.30(m, 2H), 3.45(m, 2H), 3.6(m, 4H), 3.9(m, 4H), 4.2–4.4 (m, 5H), 4.59(d, J=8.31, 1H), 4.81(t, J=9.77, 1H), 5.01(d, J=2.93, 1H), 5.12(t, J=9.77, 1H), 6.68(d, J=4.4, 1H), 7.60(m, 2H), 7.70(m, 1H), 7.83(d, J=8.31, 2H), 8.02(d, J=7.82, 2H), 8.23(d, J=5.86, 1H); $^{13}$C NMR(DMSO-d$_6$, 300 MHz) δ 16.71(q), 18.56(q), 20.24(q), 20.72(q), 22.57(q), 24.30(t), 30.36(q), 47.12(d), 53.67(t), 54.09(d), 58.09(t), 61.61(t), 62.45(t), 68.01(d), 68.33(d), 70.31(d), 72.37(d), 74.86(d), 75.76(d), 76.73(d), 89.73(d), 89.54(d), 124.84(d), 127.68(d), 129.40(d), 133.98(d), 139.30(s), 169.25(s), 169.36(s), 169.42(s), 169.54(s), 169.89(s), 169.98(s), 171.52(s), 173.90(s). HRMS calcd for C$_{38}$H$_{54}$N$_3$O$_{20}$S, 904.3021, found 904.3011.

II. Preparation of the Monophosphate Triester Intermediate (Compound xxii):

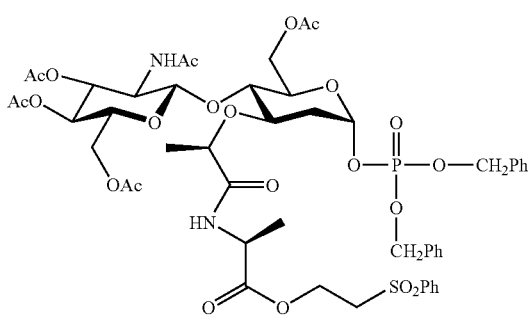

Compound xxi (1.4 g, 1.55 mmol) in anhydrous dichloromethane (10 mL) is added rapidly via syringe to a vigorously stirred suspension of tetrazole (517 mg, 7.31 mmol) and dibenzyl N,N'-diethylphosphoramidite (1.4 mL, 4.70 mmol) in anhydrous dichloromethane (10 mL) under argon at 25° C. The reaction mixture becomes homogeneous within a few minutes. After 2 h, thin layer chromatography (10% MeOH/CHCl$_3$) shows a complete reaction. The mixture is diluted with dichloromethane (10 mL), then washed with saturated NaHCO$_3$ (5 mL), water (5 mL) and brine (5 mL). The organic solution is dried over Na$_2$SO$_4$, and concentrated in vacuo to a colorless oil, which crystallized upon trituration with 1:1 diethyl ether/hexanes. The solids are filtered, dissolved in THF (30 mL), and cooled to −78° C. Hydrogen peroxide (30%, 2.8 mL) is added dropwise via syringe to the vigorously stirred solution. After the addition is complete, the ice bath is removed and the mixture allowed to warm to room temperature over 2 h. TLC (4:1 EtOAc/acetone) shows complete reaction. The mixture is diluted with ice-cold saturated Na$_2$S$_2$O$_3$ (5 mL), followed by ethyl acetate (10 mL), and stirred for 5 minutes. The organic layer is dried over MgSO$_4$ and concentrated in vacuo to a colorless oil, which produced a white solid upon trituration with 1:1 Et$_2$O/hexanes. The white solid is dried under high vacuum at 40° C. to provide the monophosphate triester product (1.4 g, 90% yield of compound xxii).

Analytical (compound xxii): $^1$H NMR(DMSO-d$_6$, 500 MHz) δ 1.10(d, 3H), 1.20(d, 3H), 1.69(s, 3H), 1.75(s, 3H), 1.92(s, 3H), 1.96(s, 9H), 3.43(m, 1H), 3.57(m, 2H), 3.61(m, 1H), 3.83(m, 4H), 4.05(m, 4H), 4.35(m, 3H), 4.60(m, 1H), 4.73(m, 1H), 4.91(t, 1H), 5.00(m, 4H), 5.24(t, 1H), 5.81(m, 1H), 7.35(m, 10H), 7.64(m, 2H), 7.74(m, 1H), 7.86(d, 2H), 8.06(d, 1H), 8.39(d, 1H), 8.66(d, 1H); Anal. Calcd for: C$_{52}$H$_{66}$N$_3$O$_{23}$PS.2H$_2$O: C, 52.04; H, 5.88; N, 3.50. Found C, 51.84; H, 5.73; N, 3.34. HRMS calcd for C$_{52}$H$_{66}$N$_3$O$_{23}$PS, 1164.3624, found 1164.3601.

III. Preparation of the Disaccharyl Pentapeptide Intermediate (Compound xxiii)

xxiii

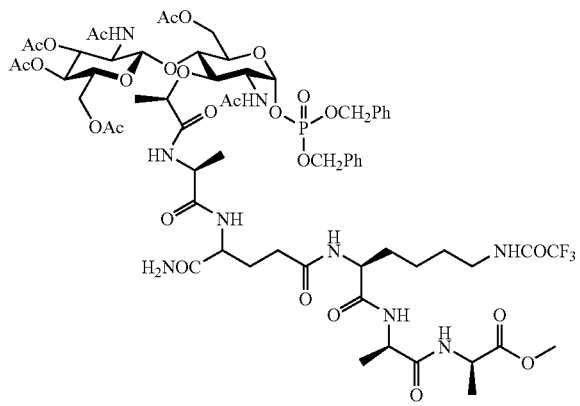

DBU (102 μL, 0.68 mmol) is added dropwise to a solution of the monophosphate triester (793 mg, 0.68 mmol of compound xxii) in dichloromethane (10 mL) under an argon atmosphere. After 15 minutes, thin layer chromatographic analysis (15% MeOH/CHCl$_3$) shows complete consumption of the starting material. The reaction solution is diluted with dichloromethane (20 mL) and washed with 1N HCl (30 mL). The organic layer is concentrated, then the resulting foam is triturated with Et$_2$O and allowed to stand at room temperature for about 2 h. After filtration, the crude acid product is dried at 40° C. for 2 h (465 mg, 68% yield).

The acid (465 mg, 0.47 mmol), N-hydroxysuccinimide (81 mg, 0.7 mmol) and EDCI (134 mg, 0.70 mmol) are dissolved in anhydrous DMF (4 mL) and allowed to stir for 18 h. Analysis of the reaction mixture by thin layer chromatography (15% MeOH/CHCl$_3$) reveals complete consumption of the starting material. The reaction mixture is concentrated in vacuo, redissolved in ethyl acetate (10 mL), then washed with water (10 mL) and brine (10 mL). The organic solution is dried with MgSO$_4$, and concentrated to a foam which, after trituration with diethyl ether (5 mL), provides the NHS-ester (398 mg, 78% yield).

The NHS-ester (398 mg, 0.34 mmol), tetrapeptide (254 mg, 0.36 mmol of compound xix) and iPr$_2$NEt (192 μL, 1.1 mmol) are dissolved in DMF (3 mL) and stirred at RT under argon for 18 h. The reaction mixture is then concentrated, dissolved in isopropanol/chloroform (1:9, 10 mL), washed with brine (3×5 mL), dried with MgSO$_4$ and concentrated in vacuo. The resulting oil is triturated with diethyl ether to provide the disaccharyl pentapeptide compound xxiii (474 mg, 46% yield overall from compound xxii) as a white solid.

Analytical (compound xxiii): $^1$H NMR(DMSO-d$_6$, 500 MHz) δ 1.15–1.23(m, 12H), 1.40(m, 3H), 1.66(s, 3H), 1.69(s, 3H), 1.86(s, 3H), 1.89(s, 3H), 1.90(s, 3H), 1.91(s, 3H), 2.1(m, 2H), 3.1(m, 4H), 3.53(s, 3H), 3.71(m, 4H), 3.95(m, 3H), 4.1–4.25(m, 10H), 4.34(t, J=7.33, 1H), 4.48(d, J=6.84, 1H), 4.67(d, J=8.61, 1H), 4.84(t, J=9.77, 1H), 4.98 (m, 4H), 5.18(t, J=9.77, 1H), 5.57(m, 1H), 6.97(s, 1H), 7.25(s, 1H), 7.30(m, 10H), 7.97(m, 2H), 8.13(m, 3H), 8.15(d, J=8.30, 1H), 8.56(d, J=5.37, 1H), 9.32(m, 1H); Anal. Calculated for C$_{64}$H$_{89}$F$_3$N$_9$O$_{27}$P.0.5H$_2$O: C, 50.70; H, 5.99; N, 8.33. Found: C, 50.99; H, 6.38; N, 8.33. MS (ES$^-$) m/z 1503 (25%), 751.3 ([M−2]$^{2-}$, 100%.)

Compound xxiii can also be prepared by an alternative procedure. To a solution of the free amine of the tetrapeptide compound xx (0.068 g, 0.129 mmol) in CHCl$_3$ (1.3 mL) are added sequentially H$_2$O (1.3 mL), the acid of the disaccharide (0.128 g, 0.129 mmol), and 1-hydroxybenzotriazole (HOBt) (0.017 g, 0.129 mmol). The mixture is then cooled to 0° C. and N-ethyl-N'-[3-(dimethylamino)propyl]carbodiimide (EDCI) (0.027 g, 0.142 mmol) is added. The reaction is stirred vigorously for 2 days at 4° C. 1N HCl is added and the layers are partitioned. The organic phase is washed with 1N HCl, H$_2$O, saturated NaHCO$_3$, H$_2$O, and brine. The combined aqueous phases are extracted with CHCl$_3$ (x3). The combined organic phase is dried with Na$_2$SO$_4$ and concentrated in vacuo to an oil. The residue is purified by normal phase chromatography over silica to yield compound xxiii (57%) as a colorless solid. This alternative procedure is described in Ho, G-J; Emerson, K. M.; Mathre, D. J.; Shuman, R. F.; Grabowski, D. J. "Carbodiimide-Mediated Amide Formation in a Two-Phase System. A High-Yield and Low-Racemization Procedure for Peptide Synthesis," J. Org. Chem. 1995, 60, 3569–3570, incorporated herein by reference.

IV. Preparation of the Protected Lipid II Intermediate (Compound xxiv)

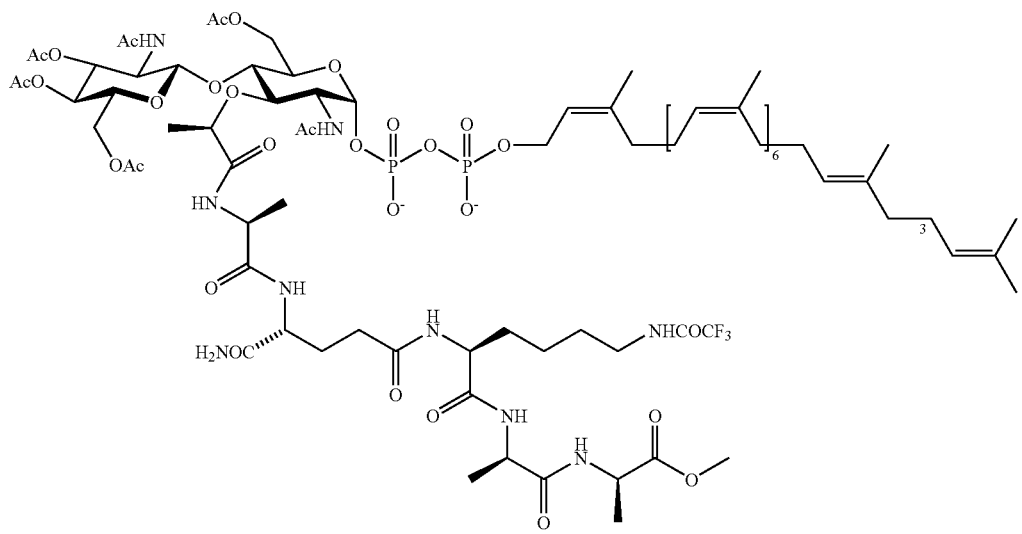

xxiv

The disaccharyl pentapeptide (53 mg, 0.035 mmol of compound xxiii) is added to a suspension of 10% Pd/C (100 mg) in methanol (6.0 mL), cooled in an ice bath to aid in degassing the reaction solution. The solution is then warmed to room temperature and hydrogenated at atmospheric pressure for 1.5 h. The catalyst is collected by filtration, and the resulting solution is treated with pyridine (1.0 mL). The resulting mixture is concentrated in vacuo to an off-white solid, which is collected and dried under high vacuum for 16 h (ESI-MS m/z 1322, [M–H]).

The off-white solid is added to a mixture of 1,1'-carbonyldiimidazole (26.0 mg, 0.16 mmol) in anhydrous DMF (2.5 mL) and anhydrous THF (2.0 mL). After stirring for 2 hours, the reaction is determined to be complete by mass spectroscopy (ESI-MS m/z 1372.4, [M–H]). Methanol (0.6 mL) is added, and the resulting solution stirred for 15 min. The mixture is then concentrated in vacuo and evaporated from pyridine (1.0 mL). The solid material obtained, is dried under high vacuum for 2 h.

The residue is dissolved in DMF (0.4 mL) and dry THF (1.6 mL), to which a solution of undecaprenyl phosphate diammonium salt (21.4 mg, 0.024 mmol of compound xx) in THF (0.5 mL) and DMF (0.1 mL) is added. 1H-tetrazole (1.8 mg, 0.03 mmol) is added and the mixture is stirred for 4 days under an argon atmosphere. Afterwards, the solution is concentrated in vacuo to give compound xxiv.

V. Preparation of Lipid II:

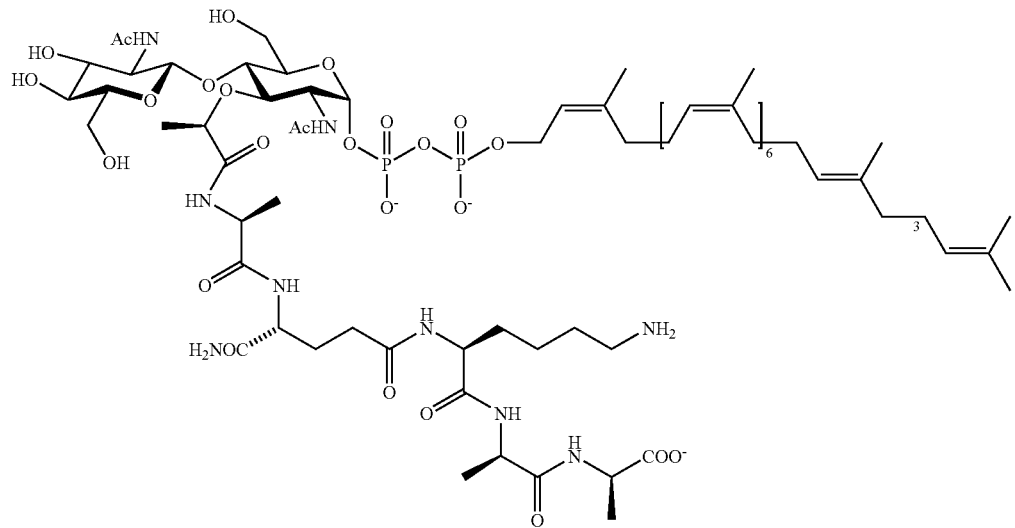

Lipid II

The residue from the previous step (compound xxiv) is dissolved in 1,4-dioxane:water (1:1; 2 mL). 1N sodium hydroxide (0.3 mL) is added and the resulting mixture stirred for 2 h. The reaction solution is filtered through an aqueous filter disc and purified by reverse phase HPLC on a Dynamax C8 100 Å, 5μ, 21.4 mm×25 cm column using a gradient elution of 15:85 A:B to 0:100 A:B over 30 min, at a flow rate of 21.6 ml/min (where A=0.05M aqueous ammonium bicarbonate and B=methanol). The retention time of the product is 18 min (detection at 214 nm). Lyophilization of the pure fractions gives 13.8 mg of Lipid II (24% yield overall from compound xxiii). Ultra High Resolution MS calcd for $C_{94}H_{157}N_9O_{25}P_2$, 1874.07659; found, 1874.08023.

Verification of Lipid II Structure

I. Biochemical Assay

The structural identity of Lipid II is validated via a biochemical assay employing a modified version of Lipid II bearing a dansyl tag on the ε-amino group of the L-lysine residue. The substrate is prepared by direct dansylation of Lipid II in analogy to the conditions disclosed in Weppner, W. A., and F. C. Neuhaus, *J. Biol. Chem.*, 252(7), 2296 (1977).

Weppner and Neuhaus had previously demonstrated the in situ generation of Lipid II by incorporating a Park nucleotide bearing a dansyl tag on the L-lysine residue into glycan strands via incubation with a membrane fraction prepared from *Gaffkya homari*. In these experiments, the glycan strands were readily detected by descending paper chromatography followed by exposure of the chromatograms to ultraviolet light. A similar experiment utilizing a membrane particulate fraction from *E. coli*. with a dansyl-tagged version of Lipid I (the immediate precursor to Lipid II that lacks the NAG carbohydrate subunit) has also been reported. See, Auger, G., et al., *Lett. Pept. Sci.*, 4, 371 (1997).

In analogous fashion, incubation of our dansyl-tagged Lipid II derivative with a monofunctional transglycosylase (MtgA) from *Staphylococcus aureus* (described in U.S. Pat. No. 5,922,540 and incorporated herein by reference) and subsequent analysis of the reaction mixtures by thin layer chromatography, under the conditions reported by Weppner and Neuhaus, results in the visualization of glycan strands upon exposure to ultraviolet light in exact analogy to the precedent cited above. (See figure)

Although a dansyl tag was used in the experiments described above, other tags well-known to those skilled in the art can also be used. As used herein, "tag" refers to an element or compound containing atoms that can be distinguished from their normal counterparts by physical means (e.g., radioactivity assay, mass spectrography or fluorescence), and can thus be used to follow (trace) the metabolism of the normal substances.

II. Protocol for Biochemical Transglycosylation

In the figure, the following protocols are used for the corresponding lanes represented in the thin layer chromatography (TLC) strip.

Lane 1: 5 mL substrate stock solution (300 mM dansyl lipid II in 75 mM PIPES at pH 6.1, 37.5 mM $MgCl_2$)

Lanes 2 and 3: Lane 1 plus 5 mL MtgA enzyme solution (10 mM stock in 25 mM HEPES at pH 7.5, 150 mM NaCl, 0.5% CHAPS); incubate 20 min @ 25° C.; stop with 30 mL methanol at 0° C.

Lane 4: Add 1 mL of lysozyme stock (1 mg/mL hen eggwhite lysozyme, HEWL)

Location of reaction products is visualized by exposing the TLC to UV light (366 nm). (See Figure)

III. Preparation of Dansylated Lipid II:

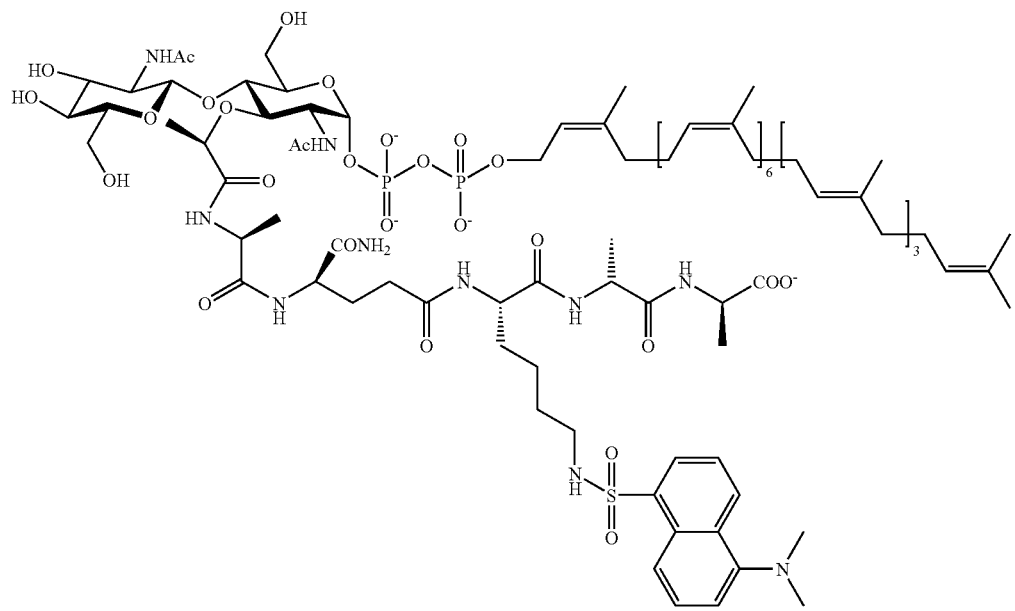

Lipid II with dansyl tag

A solution of dansyl chloride (13.8 mg, 5.1 μmol) in acetone (250 μL) is added in one portion to a solution of Lipid II (2.4 mg, 1.3 μmol) in 0.25M aq NaHCO$_3$ (250 μL). The mixture, which turns turbid immediately, is stirred at room temperature for 90 minutes. Electrospray MS and HPLC show complete conversion to product. The mixture is concentrated in vacuo, redissolved in 1:1 water/acetonitrile and purified by preparative chromatography on a Dynamax C8 column (100 Å, 5μ, 21.4 mm×25 cm) using a gradient of 85:15 to 100:0 methanol/50 mM ammonium bicarbonate over 20 minutes (detection at 214 nm). The appropriate fractions are combined and lyopholized to provide dansylated Lipid II (1.7 mg, 63% yield). Ultra High Resolution MS calcd for $C_{106}H_{168}N_{10}O_{27}P_2S$, 2107.12764; found, 2107.12725.

We claim:

1. An isolated Lipid II compound of the following formula:

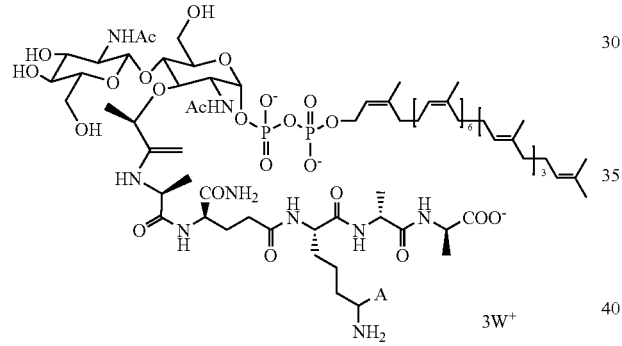

wherein:

A is a hydrogen or an carboxyl group:

Ac is —C(O)CH$_3$; and

W$^+$ is each independently a proton or cation selected from the group consisting of an alkali metal, alkaline earth metal, ammonium, alkyl ammonium, and dialkyl ammonium.

2. The isolated Lipid II compound of claim 1, wherein said Lipid II compound has a purity rater than or equal to 98%.

3. The isolated Lipid II compound of claim 1, wherein said Lipid II compound has a purity greater than or equal to 99%.

4. The isolated Lipid II compound of claim 1, wherein said Lipid II compound has a purity greater than or equal to 99.5%.

5. A process for preparing a Lipid II compound, comprising:

(1) providing a protected disaccharide core of formula 14

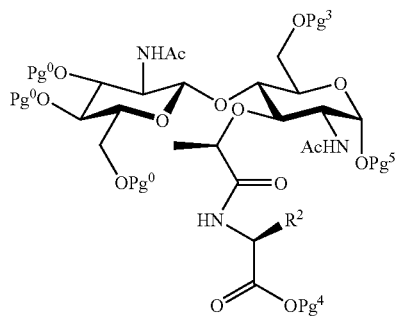

(2) introducing an anomeric phosphate to form a compound of formula 12

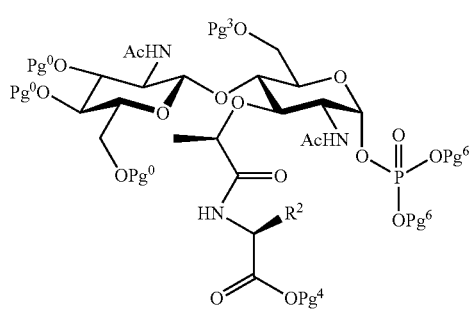

(3) introducing a polypeptide linkage to form a compound of formula 7a

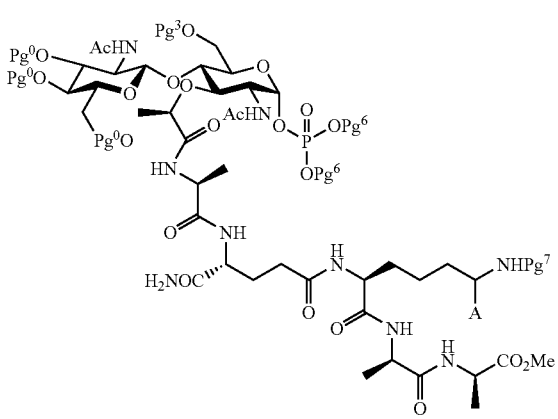

(4) introducing an undecaprenyl diphosphate linkage to form a compound of formula 8a

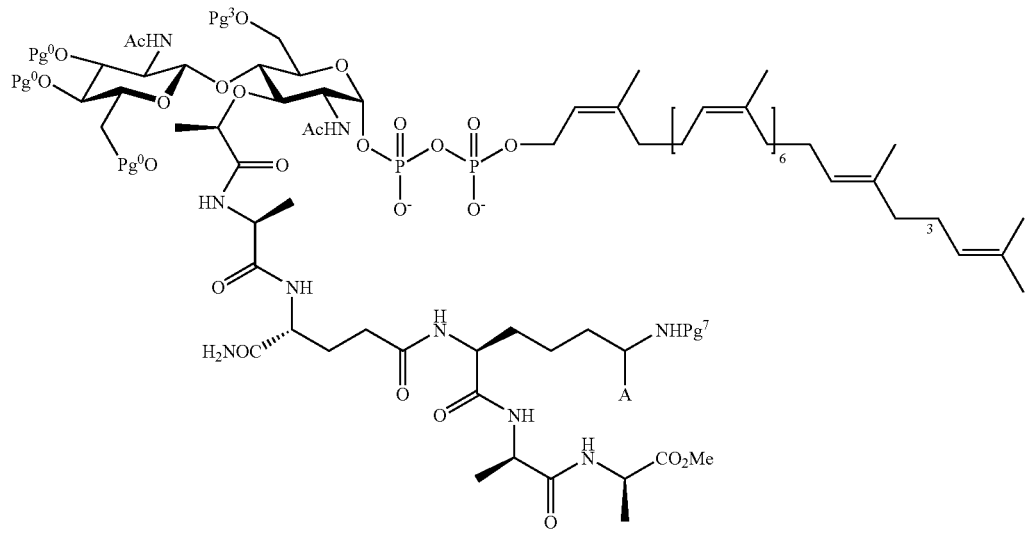

2a (5) removing Pg⁰, Pg³, Pg⁷, and Pg⁸ to form said Lipid II compound; wherein:
A is hydrogen or a carboxyl group;
R² is methyl;
Ac is —C(O)CH₃;
Pg⁰ is an acyl hydroxy-protecting group;
Pg³ is an acyl hydroxy-protecting group;
Pg⁴ is a carboxy-protecting group;
Pg⁵ is a hydroxy-protecting group;
Pg⁶ is a phosphate protecting group;
Pg⁷ is an amine-protecting group; and
Pg⁸ is a carboxy-protecting group.

6. A process for preparing purified Lipid II comprising:
chromatographically separating Lipid II analyte from a sample matrix utilizing a mobile phase maintained at a pH greater than 6; and
collecting said analyte wherein said Lipid II has a purity greater than or equal to 95%.

7. The process of claim 6 wherein said pH is between 6 and 12.

8. The process of claim 7 wherein said pH is between 7 and 10.

9. The process of claim 8 wherein said pH is between 7 and 9.

10. The process of claim 6, wherein said Lipid II has a purity greater than or equal to 95%.

11. The process of claim 6, wherein said Lipid II has a purity greater than or equal to 98%.

12. The process of claim 6, wherein said Lipid II has a purity greater than or equal to 99%.

13. A process for preparing a Lipid substrate, comprising:
(1) providing a protected disaccharide of formula 14

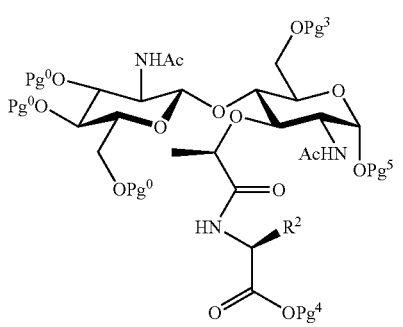

14

(2) introducing an anomeric phosphate to form a compound of formula 12

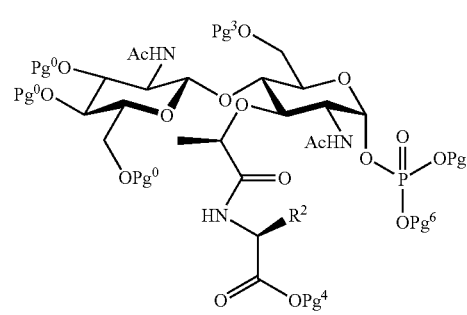

12

(3) introducing a peptide linkage to form a compound of formula 7

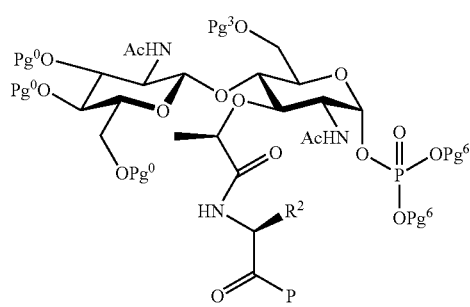

(4) introducing a lipid-carrier diphosphate linkage to form a compound of formula 2

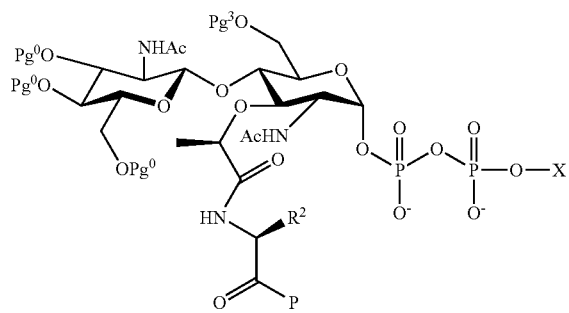

(5) removing the $Pg^0$ and $Pg^3$ groups and deprotecting the P group to produce a lipid substrate of formula 1

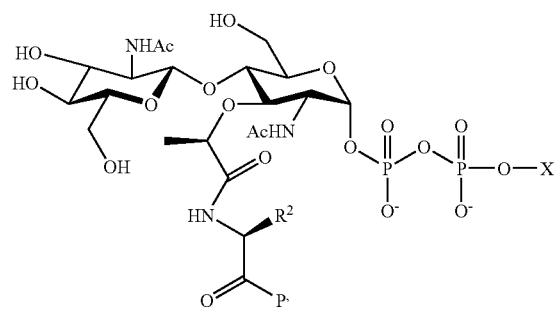

wherein:
Ac is —C(O)CH$_3$;
$Pg^0$ is acyl hydroxy-protecting group;
$Pg^3$ is an acyl hydroxy-protecting group;
$Pg^4$ is a carboxy-protecting group;
$Pg^5$ is a hydroxy-protecting group;
$Pg^6$ is a phosphate-protecting group;
$R^2$ is hydrogen, (C$_1$–C$_5$) alkyl or (C$_1$–C$_3$) alkylphenyl;
X is a lipid carrier;
P attached to the carbonyl is a residue of an amino acid or peptide, wherein P comprises a protected terminal carboxy group; and
P' is a residue of an amino acid or peptide.

* * * * *